(12) United States Patent
Flohr et al.

(10) Patent No.: US 7,750,005 B2
(45) Date of Patent: Jul. 6, 2010

(54) SUBSTITUTED HEXAHYDROPYRAZINO [1,2-A] PYRIMIDINE-4,7-DIONE DERIVATIVES, PROCESS FOR THEIR PREPARATION AND THEIR USE AS MEDICAMENTS

(75) Inventors: Stefanie Flohr, Basel (DE); Siegfried Stengelin, Eppstein (DE); Matthias Gossel, Hofheim (DE); Thomas Klabunde, Frankfurt (DE); Pavel Safar, Tucson, AZ (US); James Spoonamore, Tucson, AZ (US); Martin Smrcina, Tucson, AZ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/124,503

(22) Filed: May 21, 2008

(65) Prior Publication Data

US 2008/0221113 A1  Sep. 11, 2008

Related U.S. Application Data

(63) Continuation of application No. 10/778,554, filed on Feb. 13, 2004, now Pat. No. 7,390,814.

(60) Provisional application No. 60/480,423, filed on Jun. 20, 2003.

(30) Foreign Application Priority Data

Feb. 13, 2003 (DE) ................... 10305885
Oct. 24, 2003 (DE) ................... 10349672

(51) Int. Cl.
*C07D 487/00* (2006.01)
*A61K 31/495* (2006.01)
*A01N 43/60* (2006.01)

(52) U.S. Cl. ............ 514/246; 514/262; 514/259.1; 544/350; 544/245; 544/256

(58) Field of Classification Search ............ 514/249, 514/262, 259.1; 544/350, 245, 256
See application file for complete search history.

(56) References Cited

U.S. PATENT DOCUMENTS 6,251,902 B1   6/2001   Carpino

FOREIGN PATENT DOCUMENTS

| WO | WO 97/28265 | 7/1997 |
| WO | WO 97/41097 | 11/1997 |
| WO | WO 98/08871 | 3/1998 |
| WO | WO 99/03861 | 1/1999 |
| WO | WO 01/16135 | 3/2001 |

OTHER PUBLICATIONS

Eguchi, M., Solid-Phase Synthesis and Structural Analysis of Bicyclic B-Turn Mimetics Incorporating Functionality at i toi + 3 Positions , J. Am. Chem. Soc. 1999, vol. 121, pp. 12204-12205.

Krchnak, et al., Noninvasive Continuous Monitoring of Solid-Phase Peptide Synthesis by Acid-Base Indicator, Collect. Czech. Chem. Commun. vol. 53, (1988) pp. 2542-2548.

Tyle Praveen, Iontophoretic Devices for Drug Delivery, Pharmaceutical Research, 1986, vol. 3, No. 6, 318-326.

Vojkovsky, et al., Solid-Phase Synthesis of Heterocycles Containing an 1-Acyl-3-oxopiperazine Skeleton, J. Org. Chem.; 63; 1998; pp. 3162-3163.

*Primary Examiner*—James O. Wilson
*Assistant Examiner*—Paul V. Ward
(74) *Attorney, Agent, or Firm*—Barbara E. Kurys

(57) ABSTRACT

The invention relates to substituted hexahydropyrazino[1,2-a]pyrimidine-4,7-dione derivatives and to the physiologically tolerated salts and physiologically functional derivatives thereof.

Compounds of the formula I

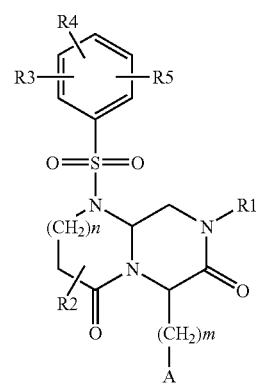

in which the radicals have the stated meanings, and the physiologically tolerated salts thereof and processes for preparing them are described. The compounds are suitable for example as anorectic agents.

2 Claims, No Drawings

SUBSTITUTED HEXAHYDROPYRAZINO [1,2-A] PYRIMIDINE-4,7-DIONE DERIVATIVES, PROCESS FOR THEIR PREPARATION AND THEIR USE AS MEDICAMENTS

This application is a continuation application of U.S. application Ser. No. 10/778,554, filed on Feb. 13, 2004, now U.S. Pat. No. 7,390,814, which claims the benefit of U.S. Provisional Application No. 60/480,423, filed Jun. 20, 2003, and claims benefit of foreign priority of German Application No. 10305885.0, filed Feb. 13, 2003, and German Application No. 10349672.6, filed Oct. 24, 2003.

The invention relates to substituted hexahydropyrazino[1,2-a]pyrimidine-4,7-dione derivatives and to the physiologically tolerated salts and physiologically functional derivatives thereof.

The invention was based on the object of providing compounds which bring about a weight reduction in mammals and are suitable for the prevention and treatment of obesity.

The invention therefore relates to compounds of the formula I,

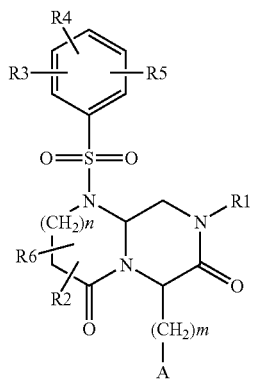

I wherein

A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 are each independently H, $(C_1-C_6)$-alkyl or a heterocycle;

n is 0 or 1;

m is 0, 1, 2, 3, 4, 5 or 6;

R1 is R8, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9 or $(C_1-C_4$-alkyl)-heterocycle, wherein the alkylene component of said $(C_1-C_6)$-alkylene-R8, $(C_2-C_6)$-alkenylene-R9, $(SO_2)$—$(C_1-C_6)$-alkylene-R8, $(SO_2)$—$(C_2-C_6)$-alkenylene-R9, (C=O)—$(C_1-C_6)$-alkylene-R8, (C=O)—$(C_2-C_6)$-alkenylene-R9, (C=O)—NH—$(C_1-C_6)$-alkylene-R8, (C=O)—NH— $(C_2-C_6)$-alkenylene-R9, COO—$(C_1-C_6)$-alkylene-R8, COO—$(C_2-C_6)$-alkenylene-R9 and alkylene-R9 groups is optionally substituted by F;

R8, R9 are each independently H, F, Cl, Br, I, OH, $CF_3$, aryl, heterocycle or $(C_3-C_8)$-cycloalkyl, wherein said aryl, heterocycle and $(C_3-C_8)$-cycloalkyl groups are optionally mono-, di- or tri-substituted by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl or $CONH_2$;

R2 is H, F, Cl, Br, I, OH, $CF_3$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl, $(C_1-C_8)$-alkylene-aryl, O—$(C_1-C_8)$-alkylene-aryl, S-aryl, CON(R11)(R12), N(R13)(R14), $(C_1-C_6)$-alkyl-N(R13)(R14), COOH, COO—$(C_1-C_6)$-alkyl, COO—$(C_2-C_6)$-alkenyl, CO—N$((C_1-C_6)$-alkyl$)_2$ or heterocycle, with the proviso that said heterocycle may not be bonded via a nitrogen atom;

R3, R4, R5 are each independently H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl$(C_1-C_8)$-alkylene-aryl, O—$(C_1-C_8)$-alkylene-aryl, S-aryl, N$((C_1-C_6)$-alkyl$)_2$, $SO_2$—$CH_3$, COOH, COO—$(C_1-C_6)$-alkyl or CO—N$((C_1-C_6)$-alkyl$)_2$;

R6 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N$((C_1-C_6)$-alkyl$)_2$, $SO_2$—$CH_3$, COOH, COO—$(C_1-C_6)$-alkyl or CO—N$((C_1-C_6)$-alkyl$)_2$;

and pharmaceutically acceptable salts thereof.

Preference is given to compounds of the formula I in which the meanings are

A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, $NO_2$, $CF_3$, $OCF_3$, CN, $(C_1-C_6)$-allyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 are each independently H, $(C_1-C_6)$-alkyl or a heterocycle;

m is 1;

n is 0 or 1;

R1 is R8, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9 or $(C_1-C_4$-alkyl)-heterocycle;

R8, R9 are each independently H, F, Cl, Br, I, OH, $CF_3$, aryl, heterocycle or $(C_3-C_8)$-cycloalkyl, wherein said aryl, heterocycle and $(C_3-C_8)$-cycloalkyl groups are optionally mono-, di- or tri-substituted by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl or $CONH_2$;

R2 is H, F, Cl, Br, I, OH, $CF_3$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, aryl, O-aryl, $(C_1$-$C_8)$-alkylene-aryl, O—$(C_1$-$C_8)$-alkylene-aryl, S-aryl, CON(R11)(R12), N(R13)(R14), $(C_1$-$C_6)$-alkyl-N(R13)(R14), COOH, COO—$(C_1$-$C_6)$-alkyl, COO—$(C_2$-$C_6)$-alkenyl, CO—N($(C_1$-$C_6)$-alkyl$)_2$ or heterocycle, with the proviso that said heterocycle may not be bonded via a nitrogen atom;

R3, R4, R5 are each independently H, F, Cl, Br, I, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, aryl, O-aryl$(C_1$-$C_8)$-alkylene-aryl, O—$(C_1$-$C_8)$-alkylene-aryl, S-aryl, N($(C_1$-$C_6)$-alkyl$)_2$, $SO_2$—$CH_3$, COOH, COO—$(C_1$-$C_6)$-alkyl or CO—N($(C_1$-$C_6)$-alkyl$)_2$;

R6 is H, F, Cl, Br, I, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, aryl, O-aryl, $(C_1$-$C_8)$-alkylene-aryl, O—$(C_1$-$C_8)$-alkylene-aryl, S-aryl, N($(C_1$-$C_6)$-alkyl$)_2$, $SO_2$—$CH_3$, COOH, COO—$(C_1$-$C_6)$-alkyl or CO—N($(C_1$-$C_6)$-alkyl$)_2$;

and pharmaceutically acceptable salts thereof.

Particular preference is given to compounds of the formula I in which the meanings are A is aryl wherein said aryl is optionally substituted by F, Cl, Br, $NO_2$, $CF_3$, $OCF_3$, CN, $(C_1$-$C_6)$-alkyl, aryl, CON(R11)(R12), N(R13)(R14), OH, O—$(C_1$-$C_6)$-alkyl, S—$(C_1$-$C_6)$-alkyl, N(R15)CO$(C_1$-$C_6)$-alkyl or COO—$(C_1$-$C_6)$-alkyl;

R11, R12, R13, R14, R15 are each independently H or $(C_1$-$C_6)$-alkyl;

m is 1;

R1 is $(C_1$-$C_6)$-alkylene-R8 or $(C_2$-$C_6)$-alkenylene-R9;

R8, R9 are each independently H, F, Cl, Br, I, OH, $CF_3$, aryl, heterocycle or $(C_3$-$C_8)$-cycloalkyl, wherein said aryl, heterocycle and $(C_3$-$C_8)$-cycloalkyl groups are optionally mono-, di-, or tri-substituted by F, Cl, Br, I, OH, $CF_3$, $NO_2$, CN, $OCF_3$, O—$(C_1$-$C_6)$-alkyl, $(C_1$-$C_6)$-alkyl, $N_2$, CON(R11)(R12), N(R13)(R14), $SO_2$—$CH_3$, COOH, COO—$(C_1$-$C_6)$-alkyl or $CONH_2$;

R2 is H, F, Cl, Br, I, OH, $CF_3$, CN, $OCF_3$, O—$(C_1$-$C_6)$-alkyl, $(C_1$-$C_6)$-alkyl, N(R3)(R14), $(C_1$-$C_6)$-alkyl-N(R13)(R14) or COO—$(C_2$-$C_6)$-alkenyl, R3 is H R4, R5 are each independently H, F, Cl, Br, OH, $CF_3$, $OCF_3$, O—$(C_1$-$C_6)$-alkyl or $(C_1$-$C_6)$-alkyl;

R6 is H;

and pharmaceutically acceptable salts thereof.

Very particular preference is given to compounds of the formula I in which the meanings are A is aryl wherein said aryl is optionally substituted by F, Cl, Br, $NO_2$, $CF_3$, $OCF_3$, CN, $(C_1$-$C_6)$-alkyl, aryl, CON(R11)(R12), N(R13)(R14), OH, O—$(C_1$-$C_6)$-alkyl, S—$(C_1$-$C_6)$-alkyl, N(R15)CO$(C_1$-$C_6)$-alkyl or COO—$(C_1$-$C_6)$-alkyl;

R11, R12, R13, R14, R15 are each independently H or $(C_1$-$C_6)$-alkyl;

m is 1;

n is 0 or 1;

R1 is $(C_1$-$C_6)$-alkyl or $(C_2$-$C_6)$-alkenyl;

R2 is H, OH, $(C_1$-$C_6)$-alkyl, COO—$(C_2$-$C_6)$-alkenyl or $(C_1$-$C_6)$-alkyl-N(R13)(R14);

R3 is H

R4 is F, Cl, Br, OH, $CF_3$, $OCF_3$, O—$(C_1$-$C_6)$-alkyl or $(C_1$-$C_6)$-alkyl;

R5 is H, F, Cl, Br, OH, $CF_3$, $OCF_3$, O—$(C_1$-$C_6)$-alkyl or $(C_1$-$C_6)$-alkyl;

R6 is H;

and pharmaceutically acceptable salts thereof.

If radicals or substituents may occur more than once in the compounds of the formula I, such as, for example, CON(R11)(R12), they may all have, independently of one another, the stated meanings and be identical or different.

The invention relates to compounds of the formula I in the form of their racemates, enantiomer-enriched mixtures and pure enantiomers, and to their diastereomers and mixtures thereof.

The alkyl, alkenyl and alkynyl radicals in the substituents A, R1, R2, R3, R4, R5, R6, R8, R9, R10, R11, R12, R13, R14, R15 may be either straight-chain, branched or optionally halogenated. The alkyl radicals in the substituents A, R1, R2, R3, R4, R5, R6, R8, R9, R10, R11, R12, R13, R14, R15 may also be cyclic.

The term "aryl" means a phenyl or naphthyl group.

Heterocycle or heterocyclic radical means ring systems which, apart from carbon, also comprise heteroatoms such as, for example, nitrogen, oxygen or sulfur. This definition also includes ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

The corresponding N-oxides of these compounds are also included, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example, F, Cl, Br, I, $CF_3$, $NO_2$, $N_3$, CN, COOH, COO$(C_1$-$C_6)$alkyl, $CONH_2$, CONH$(C_1$-$C_6)$alkyl, CON[$(C_1$-$C_6)$alkyl]$_2$, $(C_1$-$C_6)$-alkyl, $(C_2$-$C_6)$-alkenyl, $(C_2$-$C_6)$-alkynyl, O—$(C_1$-$C_6)$-alkyl, where one or more than one, or all hydrogen(s) in the alkyl radicals may be replaced by fluorine;

$PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl, $SO_2$—$(CH_2)_n$-phenyl, where n can be 0-6, and the phenyl radical may be substituted up to twice by F, Cl, Br, OH, $CF_3$, $NO_2$, CN, $OCF_3$, O—$(C_1-C_6)$-alkyl, $(C_1-C_6)$-alkyl, $NH_2$;

$C(NH)(NH_2)$, $NH_2$, NH—$(C_1-C_6)$-alkyl, $N((C_1-C_6)$-alkyl$)_2$, $NH(C_1-C_7)$-acyl, phenyl, O—$(CH_2)_n$-phenyl, where n may be 0-6, and where the phenyl ring may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of the compounds of the invention are salts of inorganic acids such as hydrochloric acid, hydrobromic acid, phosphoric, metaphosphoric, nitric, sulfamic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. The chloride salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound according to the invention of the formula I, for example an ester, which is able on administration to a mammal such as, for example, a human to form (directly or indirectly) a compound of the formula I or an active metabolite thereof.

The physiologically functional derivatives also include prodrugs of the compounds according to the invention. Such prodrugs can be metabolized in vivo to a compound according to the invention. These prodrugs may themselves be active or not.

The compounds according to the invention may also exist in various polymorphous forms, for example as amorphous and crystalline polymorphous forms. All polymorphous forms of the compounds according to the invention lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt—underlying free compound. For the prophylaxis or therapy of the abovementioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as single dose, for example as tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gun arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula (I), which are preferably isotonic with the blood of the intended recipient. These preparations are preferably adminstered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2 (6): 318 (1986) by electrotransport or iontophoresis.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure. The compounds act as melanocortin receptor agonists and are also suitable for the treatment of disturbances of wellbeing and other psychiatric indications such as, for example, depressions, anxiety states, anxiety neuroses, schizophrenia and for the treatment of disorders associated with the circadian rhythm and for the treatment of drug abuse.

They are additionally suitable for the treatment of cancer, arthritis, sleep disorders, sleep apnoea, female and male sexual disorders, inflammations, acne, pigmentation of the skin, of metabolic syndrome, disorders of steroid metabolism, skin diseases, psoriasis, mycoses, neurodegenerative diseases and Alzheimer's disease.

In a further aspect of the invention, the compounds of the formula I can be administered in combination with one or more other pharmacologically active substances which are selected, for example, from antidiabetics, antiobesity agents, active ingredients which lower blood pressure, lipid-lowering agents and active ingredients for the treatment and/or prevention of complications caused by diabetes or associated with diabetes.

Suitable antidiabetics include insulins, amylin, derivatives of GLP-1 and GLP-2 such as, for example, those disclosed in WO 98/08871 of Novo Nordisk A/S, and orally active hypoglycemic active ingredients.

The orally active hypoglycemic active ingredients preferably comprise sulfonylureas, biguanides, meglitinides, oxadiazolidinediones, thiazolidinediones, glucosidase inhibitors, glucagon receptor antagonists, GLP-1 agonists, potassium channel openers such as, for example, those disclosed in WO 97/26265 and WO 99/03861 of Novo Nordisk A/S, insulin sensitizers, activators of insulin receptor kinase, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism, such as antihyperlipidemic active ingredients and antilipidemic active ingredients, for example HMGCoA reductase inhibitors, inhibitors of cholesterol transport/of cholesterol uptake, inhibitors of bile acid reabsorption or inhibitors of the microsomal triglyceride transfer protein (MTP), compounds which reduce food intake, PPAR and RXR agonists and active ingredients which act on the ATP-dependent potassium channel of the beta cells.

In one embodiment of the invention, the present compounds are administered in combination with insulin.

In a further embodiment, the present compounds are administered in combination with a sulfonylurea such as, for example, tolbutamide, glibenclamide, glimepiride, glipizide, gliquidone, glisoxepide, glibornuride or gliclazide.

In another embodiment, the present compounds are administered in combination with a biguanide such as, for example, metformin.

In yet another embodiment, the present compounds are administered in combination with a meglitinide such as, for example, repaglinide.

In yet a further embodiment, the present compounds are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In a further embodiment the present compounds are administered in combination with an α-glucosidase inhibitor such as, for example, miglitol or acarbose.

In another embodiment, the present compounds are administered in combination with an active ingredient which acts on the ATP-dependent potassium channel of the beta cells, such as, for example, tolbutamide, glibenclamide, glimepiride, glipizide, gliclazide or repaglinide.

In yet another embodiment the present compounds are administered in combination with an antihyperlipidemic active ingredient or an antilipidemic active ingredient such as, for example, cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In a further embodiment, the present compounds are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

The compounds of the invention may additionally be administered in combination with one or more antiobesity agents or appetite-regulating active ingredients.

Active ingredients of these types may be selected from the group consisting of CART agonists, NPY antagonists, MCH antagonists, orexin antagonists, H3 antagonists, TNF agonists, CRF agonists, CRF BP antagonists, urocortin agonists, β3 agonists, MSH (melanocyte-stimulating hormone) agonists, CCK agonists, serotonin-reuptake inhibitors, mixed serotonin- and noradrenaline-reuptake inhibitors, 5HT modulators, MAO inhibitors, bombesin agonists, galanin antagonists, growth hormone, growth hormone-releasing compounds, TRH agonists, modulators of uncoupling proteins 2 or 3, leptin agonists, dopamine agonists (bromocriptine, Doprexin), lipase/amylase inhibitors, antagonists of cannabinoid receptor 1, modulators of acylation-stimulating protein (ASP), PPAR modulators, RXR modulators, hCNTF agonists or TR-β agonists.

In one embodiment of the invention, the antiobesity agent is leptin or modified leptin.

In another embodiment, the antiobesity agent is dexamphetamine or amphetamine.

In another embodiment, the antiobesity agent is fenfluramine or dexfenfluramine.

In yet another embodiment, the antiobesity agent is sibutramine or the mono- and bisdemethylated active metabolites of sibutramine.

In a further embodiment, the antiobesity agent is orlistat.

In another embodiment, the antiobesity agent is mazindol, diethylpropion or phentermine.

The present compounds may additionally be administered in combination with one or more antihypertensive active ingredients. Examples of antihypertensive active ingredients are beta blockers such as alprenolol, atenol, timolol, pindolol, propranolol and metoprolol, ACE (angiotensin converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and alpha blockers such as doxazosin, urapidil, prazosin and terazosin. Reference may furthermore be made to Remington: The Science and Practice of Pharmacy, 19-th edition, Gennaro, editor, Mack Publishing Co., Easton, Pa., 1995.

It will be appreciated that every suitable combination of the compounds of the invention with one or more of the aforementioned compounds and optionally one or more other pharmacologically active substances is to be regarded as covered by the scope of protection of the present invention.

The efficacy of the compounds was tested as follows:

Biological Test Model:

The anorectic effect was tested on female NMRI mice. After withdrawal of food for 24 hours, the test product was administered by gavage. The animals were housed singly with free access to drinking water and were offered condensed milk 30 minutes after administration of the product. The condensed milk consumption was determined every half hour for 7 hours, and the general wellbeing of the animals was observed. The measured milk consumption was compared with the vehicle-treated control animals.

TABLE 1

Anorectic effect measured as the reduction in the cumulative milk consumption of treated compared with control animals.

| Example | Oral dose [mg/kg] | Number of animals/ cumulative milk consumption of the treated animals N/[ml] | Number of animals/ cumulative milk consumption of the control animals N/[ml] | Reduction in the cumulative milk consumption as % of the control |
|---|---|---|---|---|
| 2 | 50 | 10/4.90 | 10/5.48 | 11 |

It is evident from the table that the compounds of the formula I show a good anorectic effect and are thus very suitable as antiobesity agent.

The examples and preparation methods detailed below serve to illustrate the invention without, however, restricting it.

General Processes

The starting materials used in the synthesis were purchased from chemical suppliers such as Aldrich, Acros, Sigma, Fluka, Nova Biochem, Advanced Chemtech, Bachem, Lancaster and other companies.

In the synthesis, the functional groups of the amino acid derivatives used were protected by protective groups to prevent side reactions during the coupling steps. Examples of suitable protective groups and their use are described in The Peptides, supra, 1981 and in Vol. 9, Udenfriend and Meienhofer (Editors) 1987 (included herein by reference).

General methods of solid-phase synthesis were used to prepare the compounds of the invention. Methods of this type are described for example by Steward and Young in Solid Phase Peptide Synthesis (Freeman & Co., San Francisco 1969) (included herein by reference).

Unless indicated otherwise, the compounds were synthesized using TentaGel HL12019 Resin (Rapp Polymere, Tübingen). This commercially available polymer contains a bromoacetal linker. This type of coupling can be incorporated in all types of hydroxy-tentagel by the process described by Vojkovsky, T. et al., J. Org. Chem. 1998, 63, 3162-3163, and Patek, M., Contribution to Combinatorial Chemistry 2000, London, 11.-14. Jul. 2000 (included herein by reference).

In the first synthesis step (see scheme 1 for general synthetic scheme), amine was used in DMSO to replace bromine in the bromoacetal link at an elevated temperature. Fmoc-protected amino acid was coupled onto the secondary amine produced thereby on the polymer. The coupling was effected by means of DIC/HOAt or HATU/DIEA, usually in DMF. The coupling was carried out at room temperature (RT) for 16 hours or at 55° C. for 4-5 hours. Protection by the Fmoc group was eliminated by using 50% piperidine in DMF (5+15 minutes). The substitution can be determined by measuring the amount of liberated Fmoc from the absorbance of the solution at 302 nm after elimination of the protection, the volume of the washing liquid and the weight of the polymer employed in the synthesis in accordance with the description in Krchnak, V. et al., Collect. Czech. Chem. Commun. 53 (1988) 2542 (incorporated herein by reference).

The free amino group of the structure bound to the solid phase was then coupled to Fmoc-beta-alanine (or Fmoc-alpha-amino acid or substituted beta-amino acid). The coupling was effected with N,N'-diisopropylcarbodiimide (DIC) in the presence of HOBt, usually in DMF. The completeness of the coupling was monitored by the ninhydrin test.

A protection by the Fmoc group was eliminated with 50% piperidine in DMF for 5+15 minutes. The amount of liberated Fmoc was measured from the absorbance of the solution at 302 nm after elimination of the protection, the volume of the washing liquid and the weight of the polymer employed in the synthesis.

The free amino groups of the structure bound to the solid phase was then sulfonylated with up to 2 equivalents of a suitable sulfonyl chloride/DIEA in DCM or acetonitrile.

The completeness of the sulfonylation was monitored by the ninhydrin test.

After completion of the assembly of the precursor of the linear compound on the polymer, the solid phase was washed successively with DMF and DCM or THF and dried in vacuo.

The desired compound was subjected to cyclative cleavage off with formic acid at room temperature for 18-24 hours, at 50° C. for 6 hours or by a combination of the two conditions. The polymer was filtered off and washed with DCM or formic acid. The washing liquid was introduced into the formic acid solution. The solution was evaporated. The residue was dissolved in a mixture of water and acetonitrile and freeze dried.

The dried compound was purified with HPLC with a suitable gradient of 0.1% TFA in water and acetonitrile (ACN). After collection of the peak containing the desired synthetic product, the solution of the compound was freeze dried. To confirm that the correct compound had been synthesized, the compound was subjected to a qualitative determination with electrospray mass spectrum (LC/MS) and/or an NMR analysis.

For HPLC analysis a sample of the compound was analyzed with the Beckman HPLC system (consisting of the solvent supply system 126, the programmable detector module 166 and the autosampler 507e and controlled by data station with Gold Nouveau software) using a YMC ODS-AM 4.6×250 mm column (S-5 (5 μm), YMC, Inc. Wilmington, N.C., USA) at 230 nm. With this setting, a flow rate of 1 ml/min was used and a gradient of water/0.1% TFA buffer and ACN (HPL quality) was used as eluent.

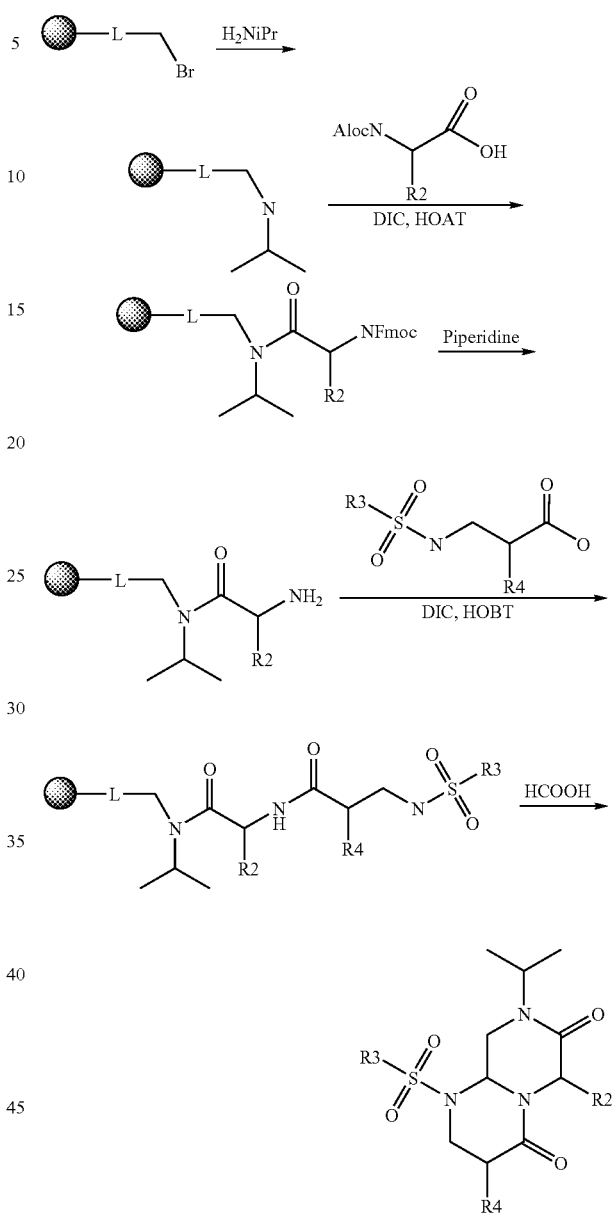

Scheme 1:

The compounds can also be prepared in solution in analogy to the described synthesis on the resin. (Scheme 2). In place of the functionalized resin, in the first stage 2-bromo-1,1-diethoxyethane is reacted with a primary amine.

Scheme 2:

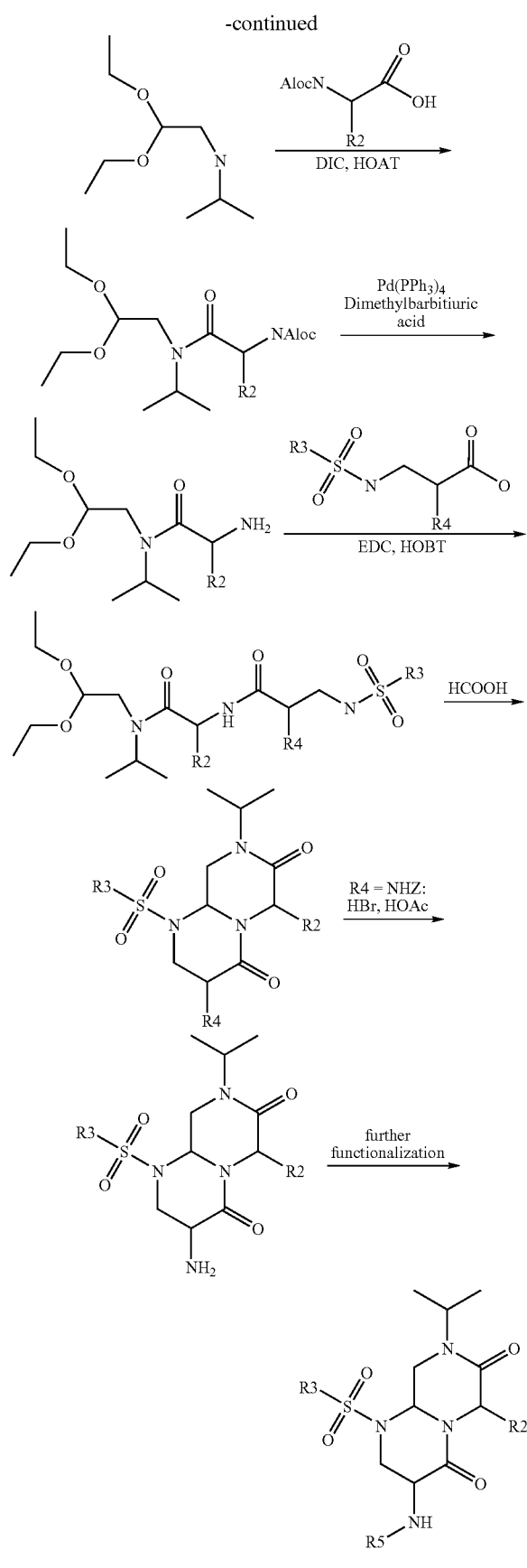

The resulting product is reacted with the amino acid in analogy to the solid-phase synthesis. The allyloxycarbonyl protective group (Aloc) can be used in place of FMOC as ammo-protective group for the amino acid, and is introduced (Aloc-Cl, triethylamine) and eliminated (Pd(PPh$_3$)$_4$, dimethylbarbituric acid) by methods known from the literature.

The amino carboxylic acid with the radical R4 is reacted with the sulfonyl chloride in the presence of triethylamine. The free carboxylic acid is coupled by the carbodiimide method (EDC, HOBt) to the free amine which has been obtained by elimination of the Aloc group. The acidic cyclization of the linear precursor obtained in this way and subsequent further functionalization proceeds in analogy to the above description.

The product was purified by developing a sample of the freeze-dried crude substance in a mixture of 0.1% strength aqueous TFA with 10-50% acetonitrile or in acetic acid. The solution of the compound was usually filtered through a syringe connected to an ACRODISC 13 CR PTFE 0.45 μm filter (Gelman Sciences; Ann Arbor, Mich., USA). An appropriate volume of the filtered solution of the compound was injected into a semipreparative C 18 column (YMC ODS-AM, S-5 (5 μm), 20×150 mm, YMC, Inc., Wilmington, N.C., USA). The flow rate of the gradient of water/0.1% TFA buffer and ACN (HPL quality) as eluent was maintained by means of the Beckman SYSTEM GOLD HPLC (System Gold, programmable solvent module 126 and programmable detector module 166, controlled by SYSTEM GOLD software). Elution of the compound was monitored by UV detection at 230 or 280 nm. After identification of the peak of the compound to be synthesized by LC/MS, the compound was collected, freeze dried and subjected to biological testing.

After purification, compounds with basic groups were obtained as trifluoroacetates. Hydrochlorides of these compounds can easily be prepared by treating the trifluoroacetate of the compound with an excess of HCl/dioxane. After evaporation of the solvents, the hydrochloride of the compound was precipitated with diethyl ether and isolated by filtration.

LC/MS was carried out with PE Sciex API 150EX and Sciex MassChrom software, equipped with a Gilson 215 liquid handler, two Shimadzu LC-10AD liquid modules, a Shimadzu SPD-10A detector, a Keystone Betasil C-18 column (2×30 mm, 3 μm, flow rate of the acetonitrile/water/0.1% TFA gradient 0.7 ml/min) in ES+ mode.

For the NMR analysis, the samples were measured in DMSO-d$_6$ (Aldrich) with a Bruker Avance DPX 300.

ABBREVIATIONS

Unless indicated otherwise, the abbreviations in the examples below have the following meaning:
ACN=Acetonitrile
Aloc=Allyloxycarbonyl
DIC=Diisopropylcarbodiimide
EDC=1-(3-Dimethylaminopropyl)-3-ethylcarbodiimide
FMOC=9-Fluorenylmethyloxycarbonyl
DCE=1,2-Dichloroethane
DIEA=Diisopropylethylamine
NaBH$_3$CN=Sodium cyanoborohydride
DMAP=N,N-Dimethylaminopyridine
DMF=N,N-Dimethylformamide
THF=Tetrahydrofuran
DIC=Diisopropylcarbodiimide
DMSO=Dimethyl sulfoxide
DCM=Dichloromethane (also referred to as methylene chloride)
HOBt=1-Hydroxybenzotriazole HOAt=1-Hydroxy-7-azabenzotriazole
HATU=Dimethylamino([1,2,3]triazolo[4,5-b]pyridin-3-yloxy)methylenedimethyl-ammonium hexafluorophosphate
HOAc=Acetic acid
$Et_3N$=Triethylamine
HCl=Hydrochloric acid
HBr=Hydrobromic acid
HPLC=High performance liquid chromatography The citation of any reference herein should not be construed as an admission that such reference is available as "Prior Art" to the instant application.

Various publications are cited herein, the disclosures of which are incorporated by reference in their entireties.

The following examples serve to explain the invention in more detail. The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the claims.

EXAMPLE 1

6-(4-Chlorobenzyl)-1-(2,4-dichlorobenzenesulfonyl)-8-isopropylhexahydropyrazino[1,2-a]pyrimidine-4,7-dione Structure:

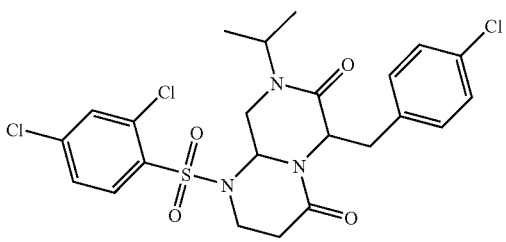

0.5 g of TentaGel HL12019 (bromoacetal linker, S=0.5 mmol/g, Rapp Polymere, Tübingen) was washed with DMSO. 20 equivalents of 2M isopropylamine solution (reagent 1) in DMSO were added, and the mixture was kept in a closed vessel at 60° C. for 15 hours. The polymer was washed 7 times with DMF.

Fmoc-4-chlorophenylalanine (reagent 2) (3 equivalents) was coupled to the secondary amine on the polymer with HOAt (3 equivalents) and DIC (3 equivalents) in DMF. The final concentration was 0.2-0.3M. The reaction mixture was left to stand at room temperature overnight. The polymer was washed 6 times with DMF. The Fmoc protective group was eliminated with 50% piperidine in DMF (5+15 minutes).

Fmoc-beta-alanine (3 equivalents) was then coupled on with HOBt (3 equivalents) and DIC (3 equivalents) in DMF (final concentration: 0.2M) over a period of at least 4 hours. The Fmoc protective group was eliminated with 50% piperidine in DMF (5+15 minutes). The polymer was washed 5 times with DMF and 4 times with DCM and mixed with a solution of 1.5 equivalents of 2,4-dichlorobenzenesulfonyl chloride (reagent 3) and 3 equivalents of DIEA in acetonitrile (final concentration: 0.1-0.15 M) and reacted at room temperature for 5 hours. It was then washed 5 times with DMF and 5 times with DCM and dried in vacuo.

For the cyclative cleavage off, the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=543.06 (calculated, monoisotopic); measured value $(M+H)^+$: 544.3.

EXAMPLE 2

6-(4-Chlorobenzyl)-1-(5-chloro-2-methoxybenzenesulfonyl)-8-isopropylhexahydropyrazino[1,2-a]pyrimidine-4,7-dione Structure:

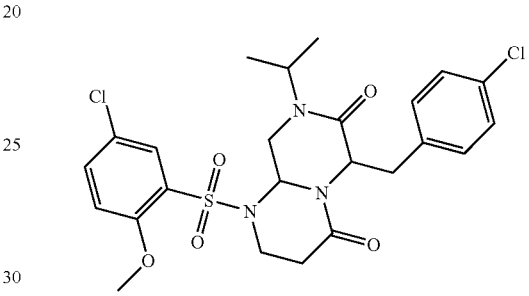

0.3 g of TentaGel HL12019 (bromoacetal linker, S=0.5 mmol/g, Rapp Polymere, Tübingen) was washed with DMSO. 20 equivalents of 2M isopropylamine solution (reagent 1) in DMSO were added, and the mixture was kept in a closed vessel at 60° C. for 15 hours. The polymer was washed 7 times with DMF.

Fmoc-4-chlorophenylalanine (reagent 2) (3 equivalents) was coupled to the secondary amine on the polymer with HATU (3 equivalents) and DIEA (9 equivalents) in DMF. The final concentration was 0.2-0.3M. The reaction mixture was left at 55° C. for 4 hours. The polymer was washed 6 times with DMF. The Fmoc protective group was eliminated with 50% piperidine in DMF (5+15 minutes).

Fmoc-beta-alanine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes).

The polymer was washed 5 times with DMF and 4 times with DCM and mixed with a solution of 1.5 equivalents of 2-methoxy-4-chlorobenzenesulfonyl chloride (reagent 3) and 3 equivalents of DIEA in acetonitrile (final concentration: 0.1-0.15M and reacted at room temperature for 5 hours. It was then washed 5 times with DMF and 5 times with THF and dried in vacuo.

For the cyclative cleavage off, the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=539.10 (calculated, monoisotopic); measured value $(M+H)^+$: 540.3.

EXAMPLE 3

6-Benzyl-1-(5-chloro-2-methoxybenzenesulfonyl)-8-isopropylhexahydropyrazino-[1,2-a]pyrimidine-4,7-dione Structure:

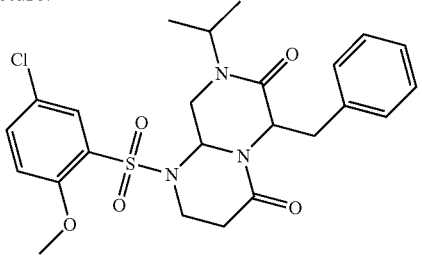

0.3 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-4-phenylalanine (3 equivalents) was coupled to the secondary amine on the polymer with HATU (3 equivalents) and DIEA (9 equivalents) in DMF. The final concentration was 0.2-0.3M. The reaction mixture was left at 55° C. for 4 hours. The polymer was washed 6 times with DMF. The Fmoc protective group was eliminated with 50% piperidine in DMF (5+15 minutes).

Fmoc-beta-alanine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes).

The polymer was washed 5 times with DMF and 4 times with DCM and mixed with a solution of 1.5 equivalents of 2-methoxy-4-chlorobenzenesulfonyl chloride and 3 equivalents of DIEA in acetonitrile (final concentration: 0.1-0.15M) and reacted at room temperature for 5 hours. It was then washed 5 times with DMF and 5 times with THF and dried in vacuo.

For the cyclative cleavage off, the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=505.14 (calculated, monoisotopic); measured value $(M+H)^+$: 506.3.

EXAMPLE 4

1-(5-Chloro-2-methoxybenzenesulfonyl)-6-(3,4-dichlorobenzyl)-8-isopropylhexahydropyrazino[1,2-a]pyrimidine-4,7-dione Structure:

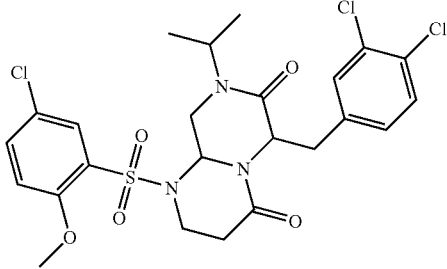

0.3 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-3,4-dichlorophenylalanine (3 equivalents) was coupled to the secondary amine on the polymer with HATU (3 equivalents) and DIEA (9 equivalents) in DMF. The final concentration was 0.2-0.3M. The reaction mixture was left at 55° C. for 4 hours. The polymer was washed 6 times with DMF. The Fmoc protective group was eliminated with 50% piperidine in DMF (5+15 minutes).

Fmoc-beta-alanine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes).

The polymer was washed 5 times with DMF and 4 times with DCM and mixed with a solution of 1.5 equivalents of 2-methoxy-4-chlorobenzenesulfonyl chloride and 3 equivalents of DIEA in acetonitrile (final concentration: 0.1-0.15M) and reacted at room temperature for 5 hours. It was then washed 5 times with DMF and 5 times with THF and dried in vacuo.

For the cyclative cleavage off, the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case, MW=573.07 (calculated, monoisotopic); measured value $(M+H)^+$: 574.3.

EXAMPLE 5

8-Allyl-1-(naphthalene-2-sulfonyl)-6-(4-nitrobenzyl)hexahydropyrazino[1,2-a]-pyrimidine-4,7-dione Structure:

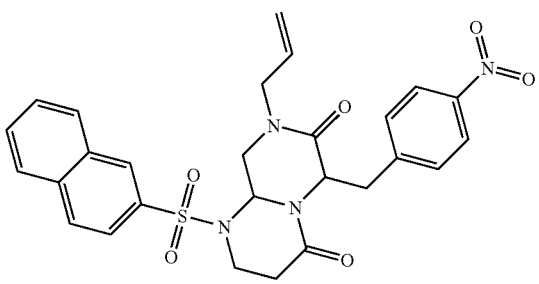

0.3 g of TentaGel HL12019 (bromoacetal linker, S=0.5 mmol/g, Rapp Polymere, Tübingen) was washed with DMSO 20 equivalents of 2M allylamine solution in DMSO were added, and the mixture was kept in a closed vessel at 60° C. for 15 hours. The polymer was washed 7 times with DMF.

Fmoc-4-nitrophenylalanine (3 equivalents) was coupled to the secondary amine on the polymer with HATU (3 equivalents) and DIEA (9 equivalents) in DMF. The final concentration was 0.2-0.3M. The reaction mixture was left at 55° C. for 4 hours. The polymer was washed 6 times with DMF. The Fmoc protective group was eliminated with 50% piperidine in DMF (5+15 minutes).

Fmoc-beta-alanine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes).

The polymer was washed 5 times with DMF and 4 times with DCM and mixed with a solution of 1.5 equivalents of 2-naphthylsulfonyl chloride and 3 equivalents of DIEA in acetonitrile (final concentration: 0.1-0.15M) and reacted at room temperature for 5 hours. It was then washed 5 times with DMF and 5 times with THF and dried in vacuo. For the cyclative cleavage off the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=534.16 (calculated, monoisotopic); measured value (M+H)$^+$: 535.3.

EXAMPLE 6

6-(4-Chlorobenzyl)-1-(5-chloro-2-methoxybenzene-sulfonyl)-3-hydroxy-8-isopropyl-hexahydropyrazino[1,2-a]pyrimidine-4,7-dione Structure:

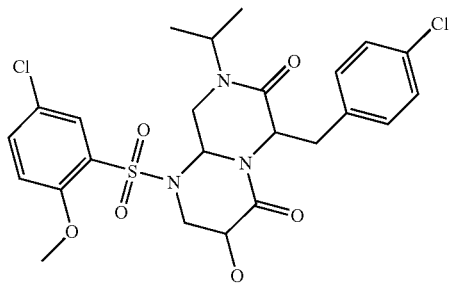

0.5 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-4-chlorophenylalanine (3 equivalents) was coupled to the secondary amine on the polymer with HOAt (3 equivalents) and DIC (3 equivalents) in DMF. The final concentration was 0.2-0.3M. The reaction mixture was left overnight at room temperature. The polymer was washed 6 times with DMF. The Fmoc protective group was eliminated with 50% piperidine in DMF (5+15 minutes).

Fmoc-isoserine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes). The polymer was washed 5 times with DMF and 4 times with DCM and mixed with a solution of 1.5 equivalents of 2-methoxy-5-chlorobenzene-sulfonyl chloride and 3 equivalents of DIEA in DCM (final concentration: 0.1-0.15M) and reacted at room temperature for 5 hours. It was then washed 5 times with DMF and 5 times with DCM and dried in vacuo.

For the cyclative cleavage off, the dry polymer was mixed with 10 ml of formic acid and shaken at room temperature for 16 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=555.10 (calculated, monoisotopic); measured value (M+H)$^+$: 556.3

EXAMPLE 7

5-(4-Chlorobenzyl)-1-(5-chloro-2-methoxybenzene-sulfonyl)-7-isopropyltetrahydro-imidazo[1,2-a]pyrazine-3,6-dione Structure:

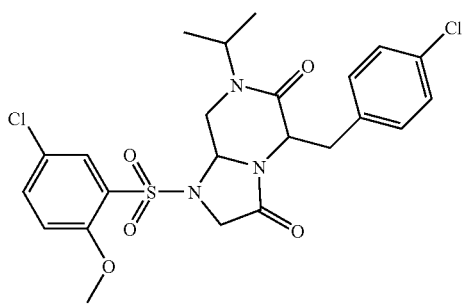

0.3 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-4-chlorophenylalanine (3 equivalents) was coupled to the secondary amine on the polymer with HOAt (3 equivalents) and DIC (3 equivalents) in DMF. The final concentration was 0.2-0.3M. The reaction mixture was left overnight at room temperature. The polymer was washed 6 times with DMF. The Fmoc protective group was eliminated with 50% piperidine in DMF (5+15 minutes).

Fmoc-glycine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes). The polymer was washed 5 times with DMF and 4 times with acetonitrile and mixed with a solution of 1.5 equivalents of 2-methoxy-4-chlorobenzene-sulfonyl chloride and 3 equivalents of DIEA in acetonitrile (final concentration: 0.1-0.15M) and reacted at room temperature for 5 hours. It was then washed 5 times with DMF and 5 times with DCM and dried in vacuo.

For the cyclative cleavage off, the dry polymer was mixed with 10 ml of formic acid and shaken at room temperature for 24 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=525.09 (calculated, monoisotopic); measured value (M+H)$^+$: 526.3.

EXAMPLE 8

5-(4-Chlorobenzyl)-1-(5-chloro-2-methoxybenzene-sulfonyl)-7-isopropyl-2-methyl-tetrahydroimidazo[1,2-a]pyrazine-3,6-dione Structure:

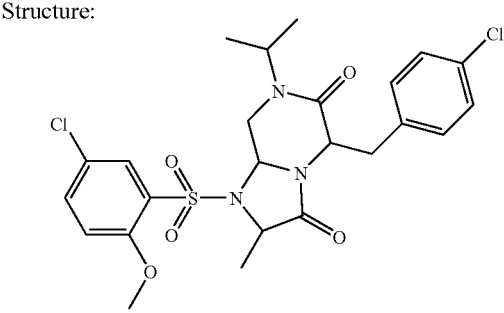

0.3 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-4-chlorophenylalanine (3 equivalents) was coupled to the secondary amine on the polymer with HOAt (3 equivalents) and DIC (3 equivalents) in DMF. The final concentration was 0.2-0.3M. The reaction mixture was left overnight at room temperature. The polymer was washed 6 times with DMF. The Fmoc protective group was eliminated with 50% piperidine in DMF (5+15 minutes).

Fmoc-(R)-alanine (3 equivalents) was then coupled on with HOBt (3 equivalents) and DIC (3 equivalents) in DMF (final concentration: about 0.2M) over a period of at least 4 hours. The Fmoc protective group was eliminated with 50% piperidine in DMF (5+15 minutes). The polymer was washed 5 times with DMF and 4 times with acetonitrile and mixed with a solution of 1.5 equivalents of 2-methoxy-4-chlorobenzenesulfonyl chloride and 3 equivalents of DIEA in acetonitrile (final concentration: 0.1-0.15M) and reacted at room temperature for 5 hours. It was then washed 5 times with DMF and 5 times with DCM and dried in vacuo.

For the cyclative cleavage off, the dry polymer was mixed with 10 ml of formic acid and shaken at room temperature for 24 hours. The polymer was filtered off and washed with DCM. The combined filtrates were evaporated in vacuo. The crude substance was dissolved in a mixture of acetonitrile and water and freeze dried. The pure title compound was removed after purification by HPLC. The system and processes described under "General processes" were used in this case. MW=539.10 (calculated, monoisotopic); measured value (M+H)+: 540.3.

EXAMPLE 9

1-(5-Chloro-2-methoxybenzenesulfonyl)-6-cyclohexylmethyl-8-isopropylhexahydropyrazino[1,2-a]pyrimidine-4,7-dione Structure:

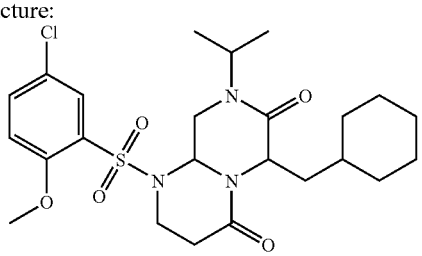

The compound in Example 9 was synthesized by the process described in Example 2 using the following reagents:

Reagent 1: isopropylamine

Reagent 2: Fmoc-cyclohexylalanine

Reagent 3: 2-methoxy-5-chlorobenzenesulfonyl chloride

MW=511.19 (calculated, monoisotopic); measured value (M+H)+: 512.3.

EXAMPLE 10

1-(5-Chloro-2-methoxybenzenesulfonyl)-6-cyclohexyl-8-isopropylhexahydropyrazino[1,2-a]pyrimidine-4,7-dione Structure:

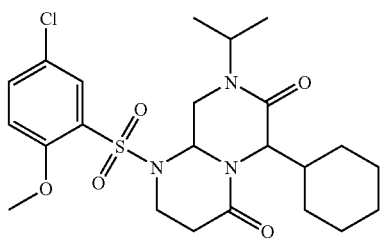

The compound in Example 10 was synthesized by the process described in Example 2 using the following reagents:

Reagent 1: isopropylamine

Reagent 2: Fmoc-cyclohexylglycine

Reagent 3: 2-methoxy-5-chlorobenzenesulfonyl chloride

MW=497.18 (calculated, monoisotopic); measured value (M+H)+: 498.3.

EXAMPLE 11

1-(5-Chloro-2-methoxybenzenesulfonyl)-8-isopropyl-6-phenethylhexahydro-pyrazino[1,2-a]pyrimidine-4,7-dione Structure:

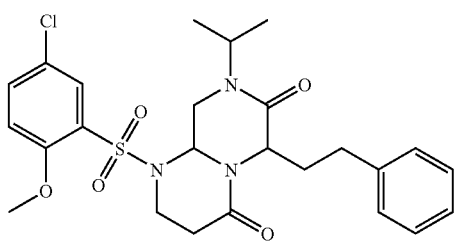

The compound in Example 11 was synthesized by the process described in Example 2 using the following reagents:

Reagent 1: isopropylamine

Reagent 2: Fmoc-homophenylalanine

Reagent 3: 2-methoxy-5-chlorobenzenesulfonyl chloride

MW=519.18 (calculated, monoisotopic); measured value (M+H)+: 520.3.

EXAMPLE 12

1-(5-Chloro-2-methoxybenzenesulfonyl)-6-indan-1-yl-8-isopropylhexahydropyrazino[1,2-a]pyrimidine-4,7-dione Structure:

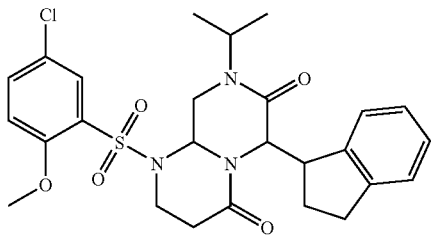

The compound in Example 12 was synthesized by the process described in Example 2 using the following reagents:

Reagent 1: isopropylamine

Reagent 2: Fmoc-indanylglycine

Reagent 3: 2-methoxy-5-chlorobenzenesulfonyl chloride
MW=531.16 (calculated, monoisotopic); measured value (M+H)$^+$: 532.3.

EXAMPLE 13

1-(5-Chloro-2-methoxybenzenesulfonyl)-6-[2-(4-hydroxyphenyl-ethyl]-8-isopropyl-hexahydropyrazino[1,2-a]pyrimidine-4,7-dione Structure:

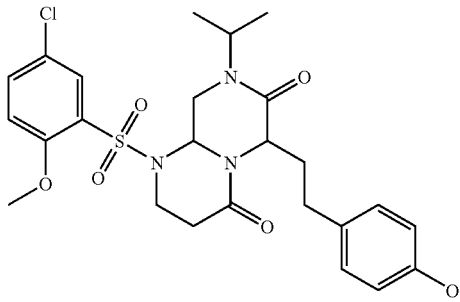

The compound in Example 13 was synthesized by the process described in Example 2 using the following reagents:

Reagent 1: isopropylamine

Reagent 2: Fmoc-homotyrosine

Reagent 3: 2-methoxy-5-chlorobenzenesulfonyl chloride
MW=535.15 (calculated, monoisotopic); measured value (M+H)$^+$: 536.3.

EXAMPLE 14

8-Isopropyl-6-(4-methoxybenzyl)-1-(2-methoxy-5-methylbenzenesulfonyl)hexahydro-pyrazino[1,2-a]pyrimidine-4,7-dione Structure:

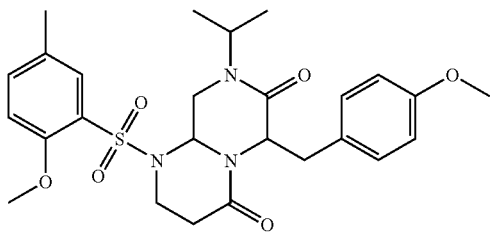

The compound in Example 14 was synthesized by the process described in Example 2 using the following reagents:

Reagent 1: isopropylamine

Reagent 2: Fmoc-O-methyltyrosine

Reagent 3: 2-methoxy-5-methylbenzenesulfonyl chloride
MW=515.21 (calculated, monoisotopic); measured value (M+H)$^+$: 516.3.

EXAMPLE 15

6-(4-Fluorobenzyl)-8-isopropyl-1-(2-methoxy-5-methylbenzenesulfonyl)hexahydro-pyrazino[1,2-a]pyrimidine-4,7-dione Structure:

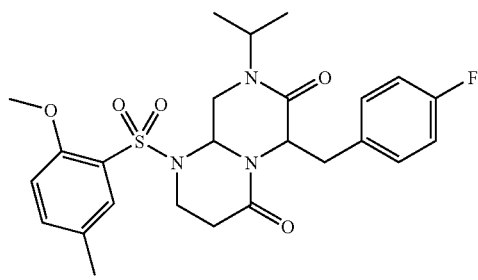

The compound in Example 15 was synthesized by the process described in Example 2 using the following reagents:

Reagent 1: isopropylamine

Reagent 2: Fmoc-4-fluorophenylalanine

Reagent 3: 2-methoxy-5-methylbenzenesulfonyl chloride
MW=503.19 (calculated, monoisotopic); measured value (M+H)$^+$: 504.3.

EXAMPLE 16

8-Isopropyl-1-(2-methoxy-5-methylbenzenesulfonyl)-6-(4-methylbenzyl)hexahydro-pyrazino[1,2-a]pyrimidine-4,7-dione Structure:

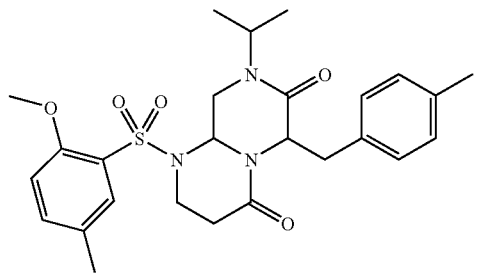

The compound in Example 16 was synthesized by the process described in Example 2 using the following reagents:

Reagent 1: isopropylamine

Reagent 2: Fmoc-4-methylphenylalanine

Reagent 3: 2-methoxy-5-methylbenzenesulfonyl chloride
MW=499.21 (calculated, monoisotopic); measured value (M+H)$^+$: 500.3.

EXAMPLE 17

6-(4-Bromobenzyl)-1-(5-chloro-2-methoxybenzene-sulfonyl)-8-isopropylhexahydropyrazino[1,2-a]pyrimidine-4,7-dione Structure:

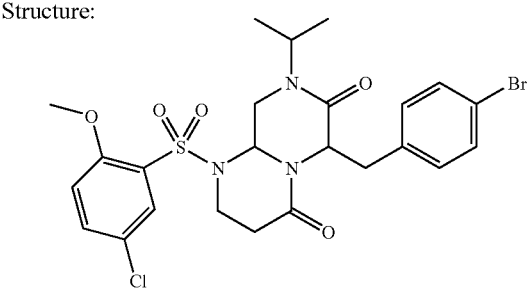

The compound in Example 17 was synthesized by the process described in Example 2 using the following reagents:

Reagent 1: isopropylamine

Reagent 2: Fmoc-4-bromophenylalanine

Reagent 3: 2-methoxy-5-methylbenzenesulfonyl chloride
MW=583.05 (calculated, monoisotopic); measured value (M+H)$^+$: 584.3.

EXAMPLE 18

1-(5-Chloro-2-methoxybenzenesulfonyl)-6-(4-fluorobenzyl)-8-isopropylhexahydropyrazino[1,2-a]pyrimidine-4,7-dione Structure:

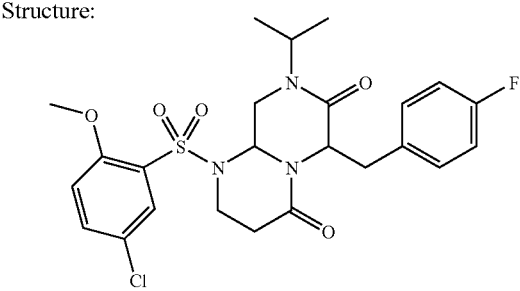

The compound in Example 18 was synthesized by the process described in Example 2 using the following reagents:

Reagent 1: isopropylamine

Reagent 2: Fmoc-4-fluorophenylalanine

Reagent 3: 2-methoxy-5-chlorobenzenesulfonyl chloride
MW=523.13 (calculated, monoisotopic); measured value (M+H)$^+$: 524.3.

EXAMPLE 19

1-(5-Chloro-2-methoxybenzenesulfonyl)-8-isopropyl-6-(4-methylbenzyl)hexahydro-pyrazino[1,2-a]pyrimidine-4,7-dione Structure:

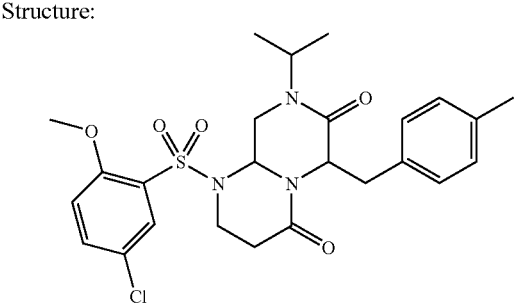

The compound in Example 19 was synthesized by the process described in Example 2 using the following reagents:

Reagent 1: isopropylamine

Reagent 2: Fmoc-4-methylphenylalanine

Reagent 3: 2-methoxy-5-chlorobenzenesulfonyl chloride
MW=519.16 (calculated, monoisotopic); measured value (M+H)$^+$: 520.3.

EXAMPLE 20

1-(4-Bromo-2-ethylbenzenesulfonyl)-8-isopropyl-6-(4-methoxybenzyl)hexahydro-pyrazino[1,2-a]pyrimidine-4,7-dione Structure:

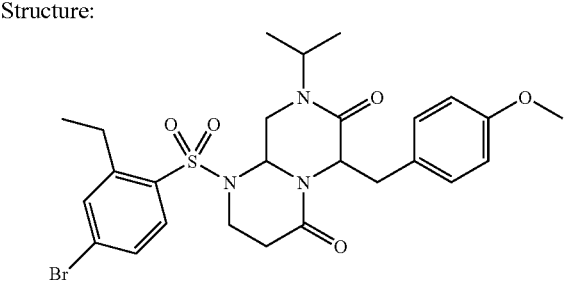

The compound in Example 20 was synthesized by the process described in Example 2 using the following reagents:

Reagent 1: isopropylamine

Reagent 2: Fmoc-O-methyltyrosine

Reagent 3: 2-ethyl-4-bromobenzenesulfonyl chloride
MW=577.12 (calculated, monoisotopic); measured value (M+H)$^+$: 578.3.

EXAMPLE 21

6-(4-Bromobenzyl)-1-(4-bromo-2-ethylbenzene-sulfonyl)-8-isopropylhexahydropyrazino[1,2-a]pyrimidine-4,7-dione Structure:

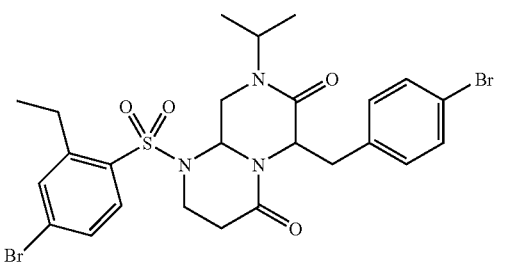

The compound in Example 21 was synthesized by the process described in Example 2 using the following reagents:

Reagent 1: isopropylamine

Reagent 2: Fmoc-4-bromophenylalanine

Reagent 3: 2-ethyl-4-bromobenzenesulfonyl chloride
MW=625.02 (calculated, monoisotopic); measured value (M+H)$^+$: 626.4.

EXAMPLE 22

1-(4-Bromo-2-ethylbenzenesulfonyl)-6-(4-fluorobenzyl)-8-isopropylhexahydropyrazino[1,2-a]pyrimidine-4,7-dione Structure:

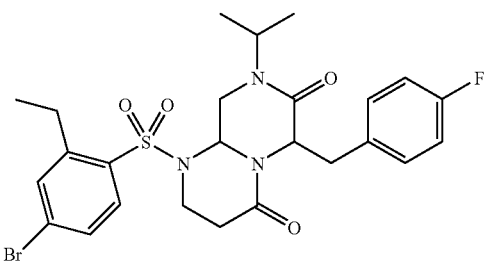

The compound in Example 22 was synthesized by the process described in Example 2 using the following reagents:

Reagent 1: isopropylamine

Reagent 2: Fmoc-4-fluorophenylalanine

Reagent 3: 2-ethyl-4-bromobenzenesulfonyl chloride
MW=565.10 (calculated, monoisotopic); measured value (M+H)$^+$: 566.3.

EXAMPLE 23

1-(4-Bromo-2-ethylbenzenesulfonyl)-8-isopropyl-6-(4-methylbenzyl)hexahydro-pyrazino[1,2-a]pyrimidine-4,7-dione Structure:

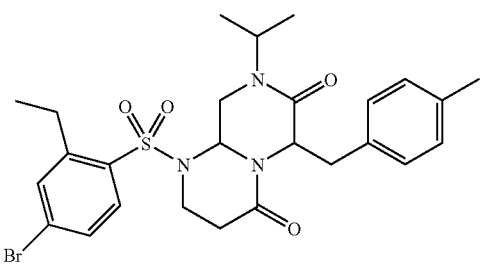

The compound in Example 23 was synthesized by the process described in Example 2 using the following reagents:

Reagent 1: isopropylamine

Reagent 2: Fmoc-4-methylphenylalanine

Reagent 3: 2-ethyl-4-bromobenzenesulfonyl chloride
MW=561.13 (calculated, monoisotopic); measured value (M+H)$^+$: 562.3.

EXAMPLE 24

8-Isopropyl-6-(4-methoxybenzyl)-1-(3-trifluoromethylbenzenesulfonyl)hexahydro-pyrazino[1,2-a]pyrimidine-4,7-dione Structure:

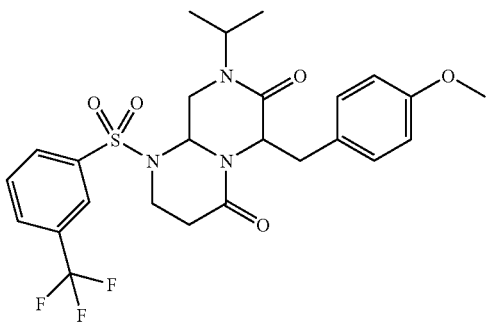

The compound in Example 24 was synthesized by the process described in Example 2 using the following reagents:

Reagent 1: isopropylamine

Reagent 2: Fmoc-O-methyltyrosine

Reagent 3: 3-trifluoromethylbenzenesulfonyl chloride
MW=539.17 (calculated, monoisotopic); measured value (M+H)$^+$: 540.3.

EXAMPLE 25

6-(4-Bromobenzyl)-8-isopropyl-1-(3-trifluoromethylbenzenesulfonyl)hexahydro-pyrazino[1,2-a]pyrimidine-4,7-dione Structure:

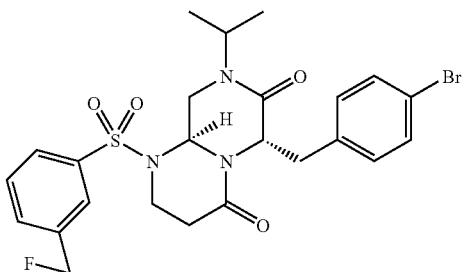

The compound in Example 25 was synthesized by the process described in Example 2 using the following reagents:

Reagent 1: isopropylamine

Reagent 2: Fmoc-4-bromophenylalanine

Reagent 3: 3-trifluoromethylbenzenesulfonyl chloride
MW=587.07 (calculated, monoisotopic); measured value (M+H)$^+$: 588.3.

EXAMPLE 26

6-(4-Fluorobenzyl)-8-isopropyl-1-(3-trifluoromethylbenzenesulfonyl)hexahydro-pyrazino[1,2-a]pyrimidine-4,7-dione Structure:

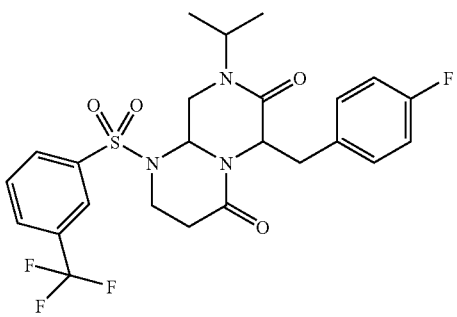

The compound in Example 26 was synthesized by the process described in Example 2 using the following reagents:

Reagent 1: isopropylamine

Reagent 2: Fmoc-4-fluorophenylalanine

Reagent 3: 3-trifluoromethylbenzenesulfonyl chloride
MW=527.15 (calculated, monoisotopic); measured value (M+H)$^+$: 528.3.

EXAMPLE 27

8-Isopropyl-6-(4-methylbenzyl)-1-(3-trifluoromethylbenzenesulfonyl)hexahydro-pyrazino[1,2-a]pyrimidine-4,7-dione Structure:

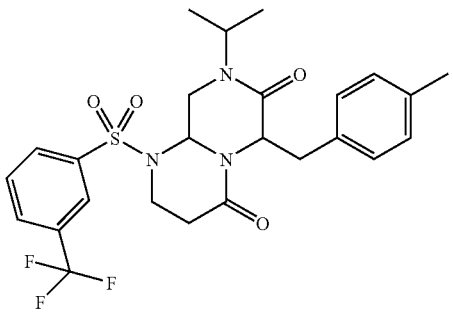

The compound in Example 27 was synthesized by the process described in Example 2 using the following reagents:

Reagent 1: isopropylamine

Reagent 2: Fmoc-4-methylphenylalanine

Reagent 3: 3-trifluoromethylbenzenesulfonyl chloride
MW=523.18 (calculated, monoisotopic); measured value (M+H)$^+$: 524.3.

EXAMPLE 28

1-(2,5-Dimethylbenzenesulfonyl-8-isopropyl-6-(4-methoxybenzyl)hexahydro-pyrazino[1,2-a]pyrimidine-4,7-dione Structure:

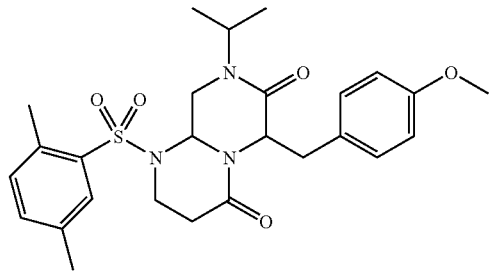

The compound in Example 28 was synthesized by the process described in Example 2 using the following reagents:

Reagent 1: isopropylamine

Reagent 2: Fmoc-O-methyltyrosine

Reagent 3: 2,5-dimethylbenzenesulfonyl chloride
MW=499.21 (calculated, monoisotopic); measured value (M+H)$^+$: 500.3.

EXAMPLE 29

6-(4-Bromobenzyl)-1-(2,5-dimethylbenzenesulfonyl)-8-isopropylhexahydropyrazino-[1,2-a]pyrimidine-4,7-dione Structure:

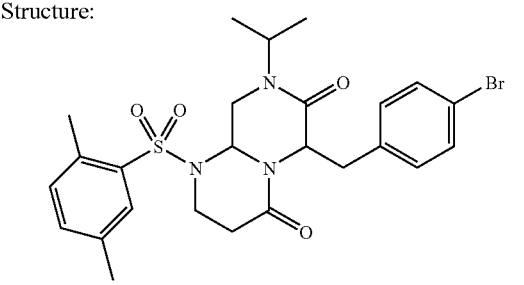

The compound in Example 29 was synthesized by the process described in Example 2 using the following reagents:

Reagent 1: isopropylamine

Reagent 2: Fmoc-4-bromophenylalanine

Reagent 3: 2,5-dimethylbenzenesulfonyl chloride
MW=547.11 (calculated, monoisotopic); measured value (M+H)$^+$: 548.3.

EXAMPLE 30

1-(2,5-Dimethylbenzenesulfonyl)-6-(4-fluorobenzyl)-8-isopropylhexahydropyrazino[1,2-a]pyrimidine-4,7-dione Structure:

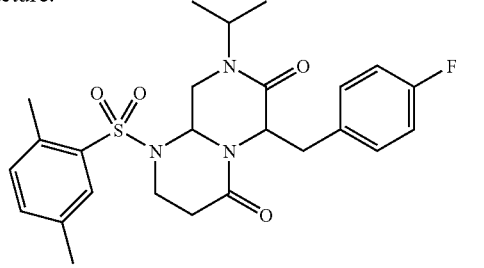

The compound in Example 30 was synthesized by the process described in Example 2 using the following reagents:

Reagent 1: isopropylamine

Reagent 2: Fmoc-4-fluorophenylalanine

Reagent 3: 2,5-dimethylbenzenesulfonyl chloride

MW=487.19 (calculated, monoisotopic); measured value (M+H)$^+$: 488.3.

EXAMPLE 31

1-(2,5-Dimethylbenzenesulfonyl)-8-isopropyl-6-(4-methylbenzyl)hexahydro-pyrazino[1,2-a]pyrimidine-4,7-dione Structure:

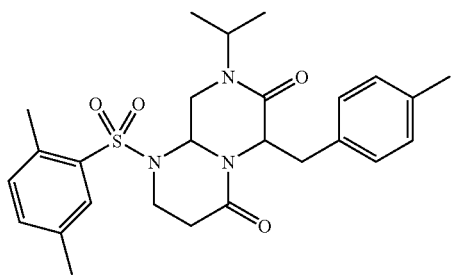

The compound in Example 31 was synthesized by the process described in Example 2 using the following reagents:

Reagent 1: isopropylamine

Reagent 2: Fmoc-4-methylphenylalanine

Reagent 3: 2,5-dimethyl benzenesulfonyl chloride

MW=483.22 (calculated, monoisotopic); measured value (M+H)$^+$: 484.3.

EXAMPLE 32

6-(4-Chlorobenzyl)-1-(4-chloro-2,5-dimethylbenzenesulfonyl)-8-isopropylhexahydropyrazino[1,2-a]pyrimidine-4,7-dione Structure:

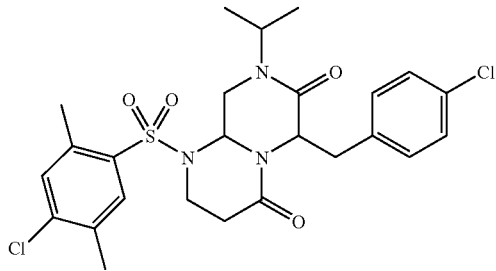

The compound in Example 32 was synthesized by the process described in Example 1 using the following reagents:

Reagent 1: isopropylamine

Reagent 2: Fmoc-4-chlorophenylalanine

Reagent 3: 4-Chloro-2,5-dimethylbenzenesulfonyl chloride

MW=537.13 (calculated, monoisotopic); measured value (M+H)$^+$: 538.3.

EXAMPLE 33

6-(4-Chlorobenzyl)-8-isopropyl-1-(2-nitrobenzenesulfonyl)hexahydropyrazino-[1,2-a]pyrimidine-4,7-dione Structure:

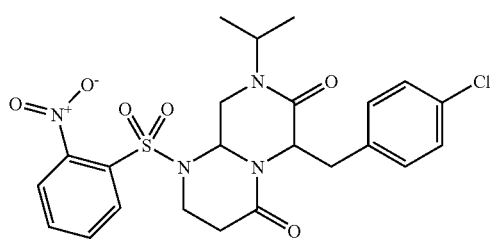

The compound in Example 33 was synthesized by the process described in Example 1 using the following reagents:

Reagent 1: isopropylamine

Reagent 2: Fmoc-4-chlorophenylalanine

Reagent 3: 2-nitrobenzenesulfonyl chloride

MW=520.12 (calculated, monoisotopic); measured value (M+H)$^+$: 521.3.

EXAMPLE 34

6-(4-Chlorobenzyl)-1-(2,4-dichloro-5-methylbenzenesulfonyl)-8-isopropylhexahydropyrazino[1,2-a]pyrimidine-4,7-dione Structure:

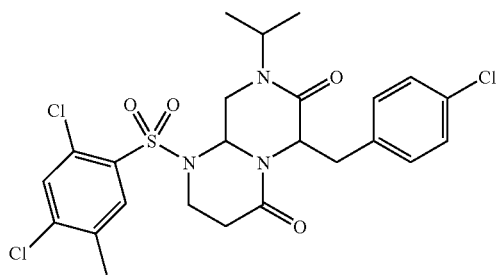

The compound in Example 34 was synthesized by the process described in Example 1 using the following reagents:

Reagent 1: isopropylamine

Reagent 2: Fmoc-4-chlorophenylalanine

Reagent 3: 2,4-dichloro-5-methylbenzenesulfonyl chloride

MW=557.07 (calculated, monoisotopic); measured value (M+H)$^+$: 558.3.

EXAMPLE 35

6-(4-Chlorobenzyl)-1-(2-chloro-4-trifluoromethyl-benzenesulfonyl)-8-isopropylhexahydropyrazino[1,2-a]pyrimidine-4,7-dione Structure:

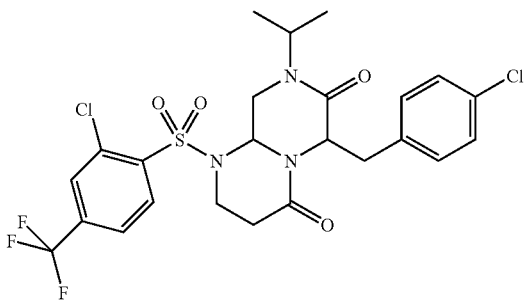

The compound in Example 35 was synthesized by the process described in Example 1 using the following reagents:

Reagent 1: isopropylamine

Reagent 2: Fmoc-4-chlorophenylalanine

Reagent 3: 2-chloro-4-trifluoromethylbenzenesulfonyl chloride

MW=557.08 (calculated, monoisotopic); measured value (M+H)$^+$: 578.3.

EXAMPLE 36

6-(4-Chlorobenzyl)-8-isopropyl-1-(2-methyl-5-nitrobenzenesulfonyl)hexahydro-pyrazino[1,2-a]pyrimidine-4,7-dione Structure:

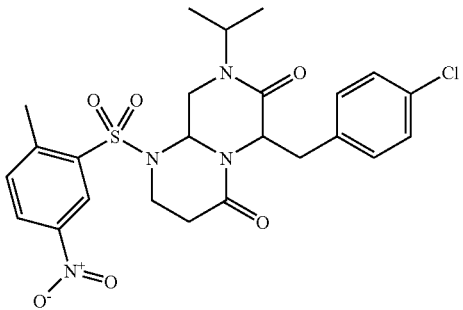

The compound in Example 36 was synthesized by the process described in Example 1 using the following reagents:

Reagent 1: isopropylamine

Reagent 2: Fmoc-4-chlorophenylalanine

Reagent 3: 2-methyl-5-nitrobenzenesulfonyl chloride

MW=534.13 (calculated, monoisotopic); measured value (M+H)$^+$: 535.3.

EXAMPLE 37

1-(4-Bromo-2-trifluoromethoxybenzenesulfonyl)-6-(4-chlorobenzyl)-8-isopropyl-hexahydropyrazino[1,2-a]pyrimidine-4,7-dione Structure:

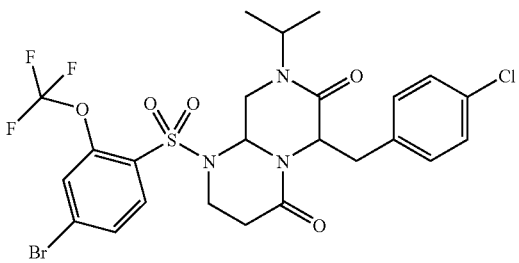

The compound in Example 37 was synthesized by the process described in Example 1 using the following reagents:

Reagent 1: isopropylamine

Reagent 2: Fmoc-4-chlorophenylalanine

Reagent 3: 4-bromobenzene-2-trifluoromethoxysulfonyl chloride

MW=637.03 (calculated, monoisotopic); measured value (M+H)$^+$: 638.4.

EXAMPLE 38

6-(1-Benzyl-1H-imidazol-4-ylmethyl)-1-(4-bromo-2-ethylbenzenesulfonyl)-8-(2-pyridin-4-ylethyl)hexahydropyrazino[1,2-a]pyrimidine-4,7-dione Structure:

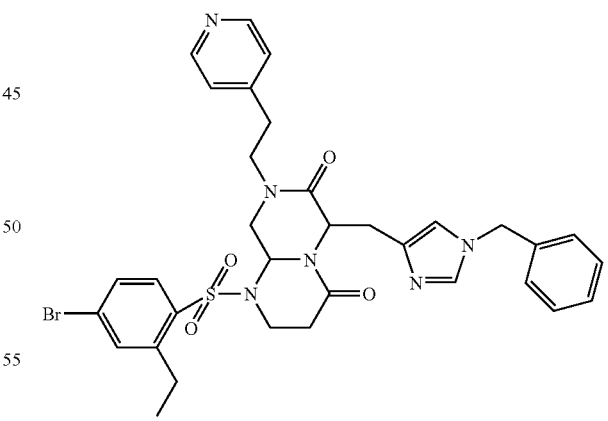

The compound in Example 38 was synthesized by the process described in Example 2 using the following reagents:

Reagent 1: 2-(4-pyridyl)ethylamine

Reagent 2: Fmoc-histidine(benzyl)

Reagent 3: 4-bromo-2-ethylbenzenesulfonyl chloride

MW=690.16 (calculated, monoisotopic); measured value (M+H)$^+$: 691.4.

EXAMPLE 39

1-(5-Chloro-2-methoxybenzenesulfonyl)-8-isopropyl-6-(4-nitrobenzyl)hexahydro-pyrazino[1,2-a]pyrimidine-4,7-dione Structure:

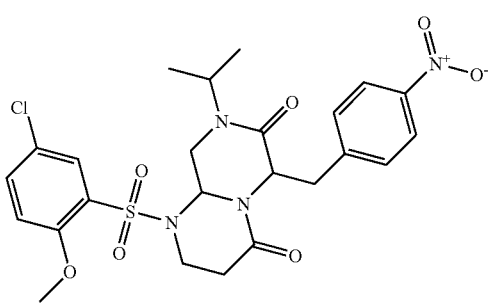

The compound in Example 39 was synthesized by the process described in Example 2 using the following reagents:

Reagent 1: isopropylamine

Reagent 2: Fmoc-4-nitrophenylalanine

Reagent 3: 2-methoxy-5-chlorobenzenesulfonyl chloride
MW=550.13 (calculated, monoisotopic); measured value (M+H)$^+$: 551.3.

EXAMPLE 40

6-(4-Chlorobenzyl)-8-isopropyl-1-(naphthalene-2-sulfonyl)hexahydropyrazino-[1,2-a]pyrimidine-4,7-dione Structure:

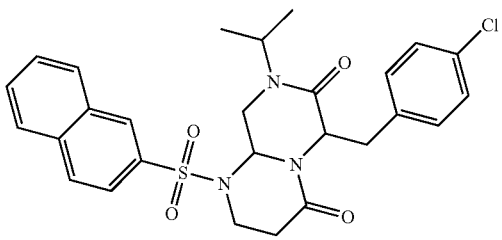

The compound in Example 40 was synthesized by the process described in Example 2 using the following reagents:

Reagent 1: isopropylamine

Reagent 2: Fmoc-4-chlorophenylalanine

Reagent 3: 2-naphthylsulfonyl chloride
MW=525.15 (calculated, monoisotopic); measured value (M+H)$^+$: 526.3.

EXAMPLE 41

6-(3,4-Dichlorobenzyl)-8-isopropyl-1-(naphthalene-2-sulfonyl)hexahydropyrazino[1,2-a]-pyrimidine-4,7-dione Structure:

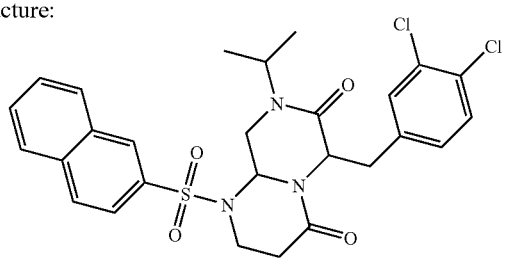

The compound in Example 41 was synthesized by the process described in Example 2 using the following reagents:

Reagent 1: isopropylamine

Reagent 2: Fmoc-3,4-dichlorophenylalanine

Reagent 3: 2-naphthylsulfonyl chloride
MW=559.11 (calculated, monoisotopic); measured value (M+H)$^+$: 560.3.

EXAMPLE 42

6-(3,4-Dichlorobenzyl)-1-(3,4-dimethoxybenzenesulfonyl)-8-isopropylhexahydropyrazino[1,2-a]pyrimidine-4,7-dione Structure:

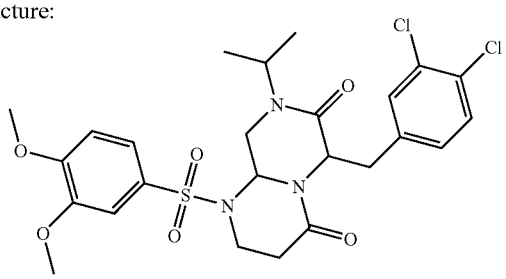

The compound in Example 42 was synthesized by the process described in Example 2 using the following reagents:

Reagent 1: isopropylamine

Reagent 2: Fmoc-3,4-dichlorophenylalanine

Reagent 3: 3,4-dimethoxybenzenesulfonyl chloride
MW=569.12 (calculated, monoisotopic); measured value (M+H)$^+$: 570.3.

EXAMPLE 43

8-Allyl-1-(4-bromo-2-ethylbenzenesulfonyl)-6-(4-chlorobenzyl)hexahydropyrazino-[1,2-a]pyrimidine-4,7-dione Structure:

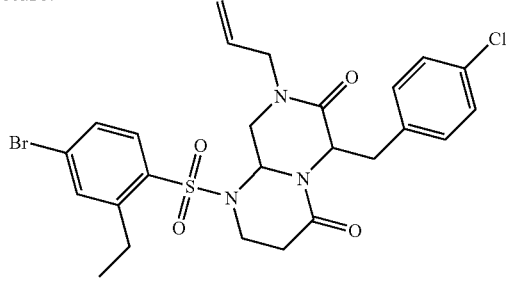

The compound in Example 43 was synthesized by the process described in Example 2 using the following reagents:

Reagent 1: allylamine

Reagent 2: Fmoc-4-chlorophenylalanine

Reagent 3: 2-ethyl-4-bromobenzenesulfonyl chloride
MW=579.06 (calculated, monoisotopic); measured value (M+H)+: 580.3.

EXAMPLE 44

8-Allyl-1-(4-bromo-2-ethylbenzenesulfonyl)-6-(4-nitrobenzyl)hexahydropyrazino-[1,2-a]pyrimidine-4,7-dione Structure:

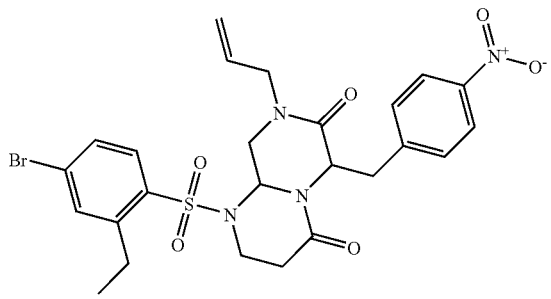

The compound in Example 44 was synthesized by the process described in Example 2 using the following reagents:

Reagent 1: allylamine

Reagent 2: Fmoc-4-nitrophenylalanine

Reagent 3: 2-ethyl-4-bromobenzenesulfonyl chloride
MW=590.08 (calculated, monoisotopic); measured value (M+H)+: 591.3.

EXAMPLE 45

8-Allyl-1-(5-chloro-2-methoxybenzenesulfonyl)-6-(3,4-dichlorobenzyl)hexahydro-pyrazino[1,2-a]pyrimidine-4,7-dione Structure:

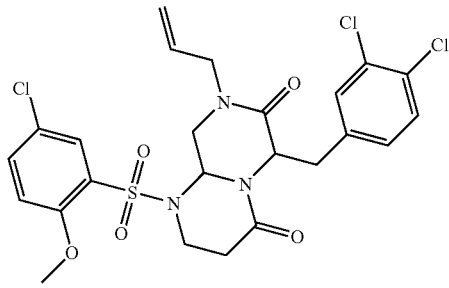

The compound in Example 45 was synthesized by the process described in Example 2 using the following reagents:

Reagent 1: allylamine

Reagent 2: Fmoc-3,4-dichlorophenylalanine

Reagent 3: 5-chloro-2-methoxybenzenesulfonyl chloride
MW=571.05 (calculated, monoisotopic); measured value (M+H)+: 572.3.

EXAMPLE 46

8-Allyl-1-(naphthalene-2-sulfonyl)-6-(4-nitrobenzyl)hexahydropyrazino[1,2-a]pyrimidine-4,7-dione Structure:

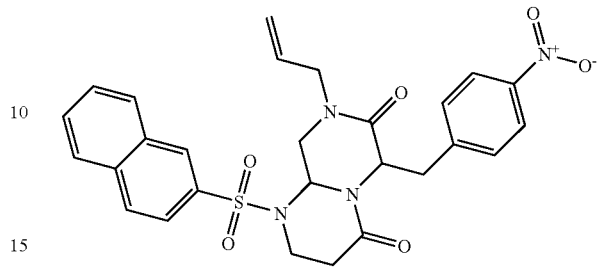

The compound in Example 46 was synthesized by the process described in Example 2 using the following reagents:

Reagent 1: allylamine

Reagent 2: Fmoc-4-nitrophenylalanine

Reagent 3: 2-naphthylsulfonyl chloride
MW=534.16 (calculated, monoisotopic); measured value (M+H)+: 535.3.

EXAMPLE 47

1-(5-Chloro-2-methoxybenzenesulfonyl)-8-isopropyl-6-pyridin-4-ylmethylhexahydro-pyrazino[1,2-a]pyrimidine-4,7-dione Structure:

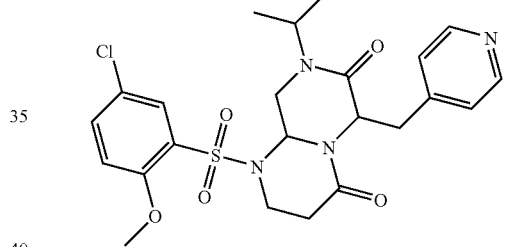

The compound in Example 47 was synthesized by the process described in Example 1 using the following reagents:

Reagent 1: isopropylamine

Reagent 2: Fmoc-4-pyridylalanine

Reagent 3: 2-methoxy-5-chlorobenzenesulfonyl chloride
MW=506.14 (calculated, monoisotopic); measured value (M+H)+: 507.3.

EXAMPLE 48

1-(5-Bromo-2-methoxybenzenesulfonyl)-6-(4-chlorobenzyl)-8-isopropylhexahydropyrazino[1,2-a]pyrimidine-4,7-dione Structure:

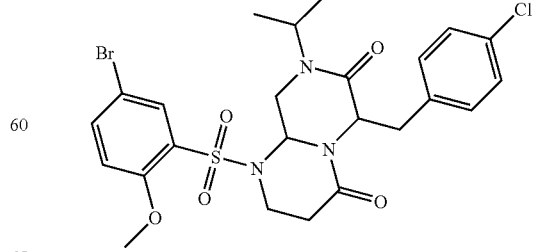

The compound in Example 48 was synthesized by the process described in Example 2 using the following reagents:

Reagent 1: isopropylamine

Reagent 2: Fmoc-4-chlorophenylalanine

Reagent 3: 5-bromo-2-methoxybenzenesulfonyl chloride
MW=583.05 (calculated, monoisotopic); measured value (M+H)+: 584.3.

EXAMPLE 49

6-(4-Chlorobenzyl)-8-isopropyl-1-(2-methoxy-5-methylbenzenesulfonyl)hexahydro-pyrazino[1,2-a]pyrimidine-4,7-dione Structure:

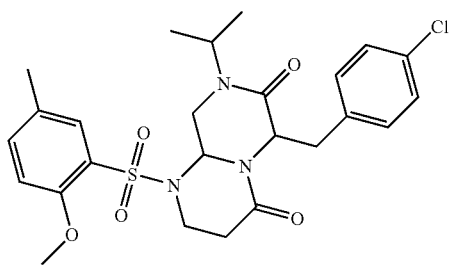

The compound in Example 49 was synthesized by the process described in Example 2 using the following reagents:

Reagent 1: isopropylamine

Reagent 2: Fmoc-4-chlorophenylalanine

Reagent 3: 2-methoxy-5-methylbenzenesulfonyl chloride
MW=519.16 (calculated, monoisotopic); measured value (M+H)+: 520.3.

EXAMPLE 50

6-(4-Chlorobenzyl)-8-isopropyl-1-(2-trifluoromethoxybenzenesulfonyl)hexahydro-pyrazino[1,2-a]pyrimidine-4,7-dione Structure:

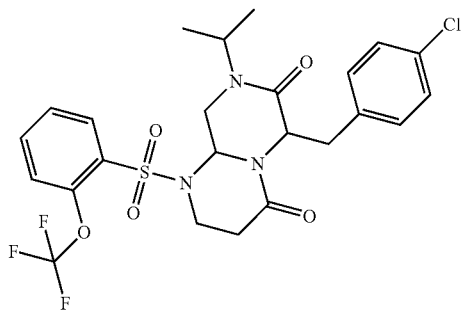

The compound in Example 50 was synthesized by the process described in Example 2 using the following reagents:

Reagent 1: isopropylamine

Reagent 2: Fmoc-4-chlorophenylalanine

Reagent 3: 2-trifluoromethoxybenzenesulfonyl chloride
MW=559.12 (calculated, monoisotopic); measured value (M+H)+: 560.3.

EXAMPLE 51

6-(4-Chlorobenzyl)-8-isopropyl-1-(2-methanesulfonylbenzenesulfonyl)hexahydro-pyrazino[1,2-a]pyrimidine-4,7-dione Structure:

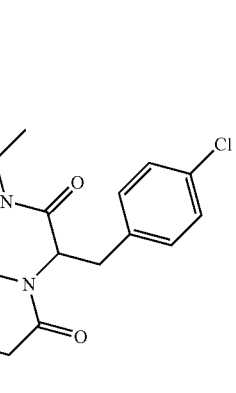

The compound in Example 51 was synthesized by the process described in Example 2 using the following reagents:

Reagent 1: isopropylamine

Reagent 2: Fmoc-4-chlorophenylalanine

Reagent 3: 2-methylsulfonylbenzenesulfonyl chloride
MW=553.11 (calculated, monoisotopic); measured value (M+H)+: 554.3.

EXAMPLE 52

3-[6-(4-Chlorobenzyl)-8-isopropyl-4,7-dioxohexahydropyrazino[1,2-a]pyrimidine-1-sulfonyl]benzonitrile Structure:

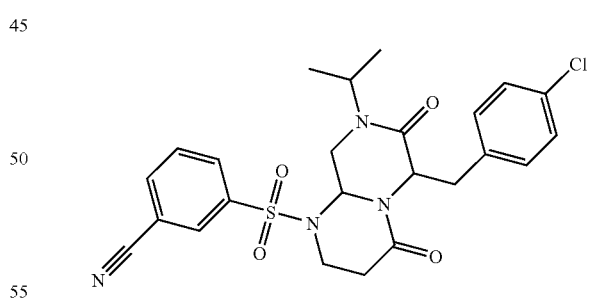

The compound in Example 52 was synthesized by the process described in Example 2 using the following reagents:

Reagent 1: isopropylamine

Reagent 2: Fmoc-4-chlorophenylalanine

Reagent 3: 3-cyanobenzenesulfonyl chloride
MW=500.13 (calculated, monoisotopic); measured value (M+H)+: 501.3.

EXAMPLE 53

6-(4-Chlorobenzyl)-8-isopropyl-1-(3-trifluoromethylbenzenesulfonyl)hexahydro-pyrazino[1,2-a]pyrimidine-4,7-dione Structure:

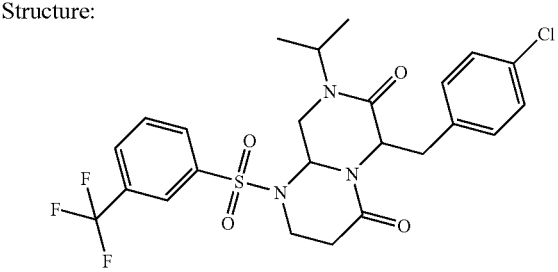

The compound in Example 53 was synthesized by the process described in Example 2 using the following reagents.

Reagent 1: isopropylamine

Reagent 2: Fmoc-4-chlorophenylalanine

Reagent 3: 3-trifluoromethylbenzenesulfonyl chloride
MW=543.12 (calculated, monoisotopic); measured value (M+H)$^+$: 544.3.

EXAMPLE 54

6-(4-Chlorobenzyl)-8-isopropyl-1-(2,4,6-trichlorobenzenesulfonyl)hexahydropyrazino-[1,2-a]pyrimidine-4,7-dione Structure:

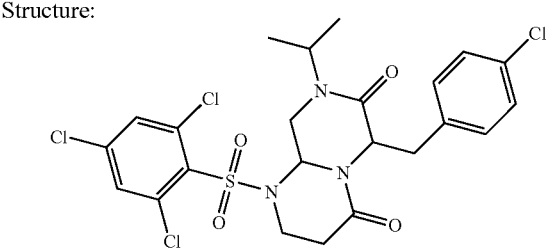

The compound in Example 54 was synthesized by the process described in Example 2 using the following reagents:

Reagent 1: isopropylamine

Reagent 2: Fmoc-4-chlorophenylalanine

Reagent 3: 2,4,6-trichlorobenzenesulfonyl chloride
MW=577.02 (calculated, monoisotopic); measured value (M+H)$^+$: 578.3.

EXAMPLE 55

6-(4-Chlorobenzyl)-1-(2,5-dimethoxybenzenesulfonyl)-8-isopropylhexahydropyrazino-[1,2-a]pyrimidine-4,7-dione Structure:

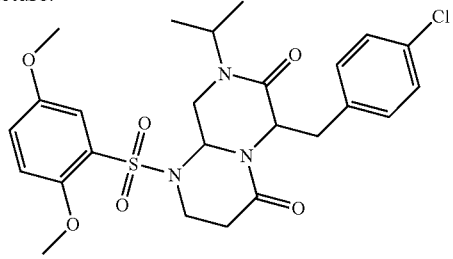

The compound in Example 55 was synthesized by the process described in Example 2 using the following reagents:

Reagent 1: isopropylamine

Reagent 2: Fmoc-4-chlorophenylalanine

Reagent 3: 2,5-dimethoxybenzenesulfonyl chloride
MW=535.15 (calculated, monoisotopic); measured value (M+H)$^+$: 536.3.

EXAMPLE 56

6-(4-Chlorobenzyl)-1-(2,5-dichlorobenzenesulfonyl)-8-isopropylhexahydropyrazino-[1,2-a]pyrimidine-4,7-dione Structure:

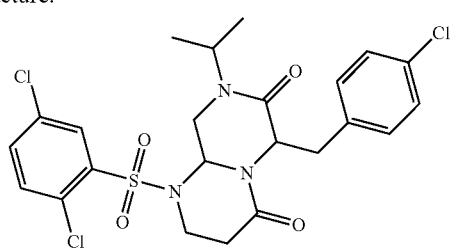

The compound in Example 56 was synthesized by the process described in Example 2 using the following reagents:

Reagent 1: isopropylamine

Reagent 2: Fmoc-4-chlorophenylalanine

Reagent 3: 2,5-dichlorobenzenesulfonyl chloride
MW=543.06 (calculated, monoisotopic); measured value (M+H)$^+$: 544.3.

EXAMPLE 57

Allyl 6-(4-chlorobenzyl)-1-(5-chloro-2-methoxybenzenesulfonyl)-8-isopropyl-4,7-dioxo-octahydropyrazino[1,2-a]pyrimidine-2-carboxylate Structure:

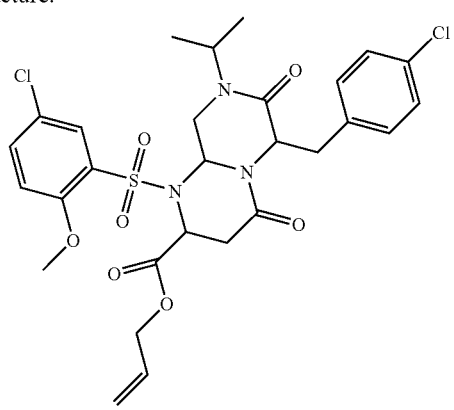

The compound in Example 57 was synthesized by the process described in Example 1 using the reagents listed below and with the following modifications:

Reagent 1: isopropylamine

Reagent 2: Fmoc-4-chlorophenylalanine
After this step and after elimination of the Fmoc protection, the coupling of Fmoc-beta-alanine from the process in Example 1 was replaced by a Fmoc-Asp(OH)—O-allyl coupling under the same conditions. After elimination of the Fmoc protection, the synthesis was continued in accordance with the process for Example 1 with reagent 3.

Reagent 3: 5-chloro-2-methoxybenzenesulfonyl chloride
MW=623.13 (calculated, monoisotopic); measured value (M+H)+: 624.4.

EXAMPLE 58

1-(5-Chloro-2-methoxybenzenesulfonyl)-8-isopropyl-6-(4-methoxybenzyl)hexahydro-pyrazino[1,2-a]pyrimidine-4,7-dione Structure:

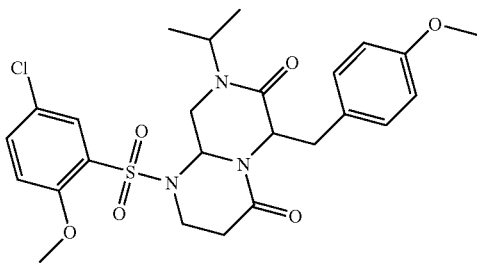

The compound in Example 58 was synthesized by the process described in Example 1 using the following reagents:

Reagent 1: isopropylamine

Reagent 2: Fmoc-O-methyltyrosine

Reagent 3: 5-chloro-2-methoxybenzenesulfonyl chloride
MW=535.15 (calculated, monoisotopic); measured value (M+H)+: 536.3

EXAMPLE 59

2-(4-Aminobutyl)-6-(4-chlorobenzyl)-1-(5-chloro-2-methoxybenzenesulfonyl)-8-isopropylhexahydropyrazino[1,2-a]pyrimidine-4,7-dione Structure:

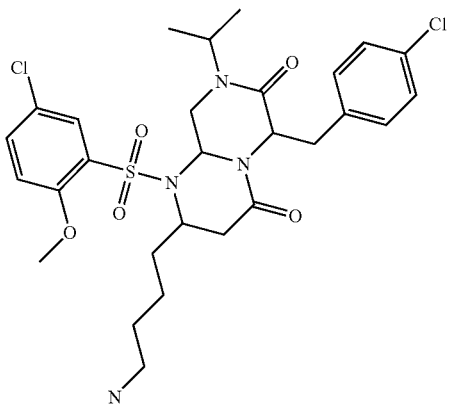

The compound in Example 59 was synthesized by the process described in Example 1 using the reagents listed below and with the following modifications:

Reagent 1: isopropylamine

Reagent 2: Fmoc-4-chlorophenylalanine

After this step and after elimination of the Fmoc protection, the coupling of Fmoc-beta-alanine from the process in Example 1 was replaced by a Fmoc-beta-homolysine(Boc) coupling under the same conditions. After elimination of the Fmoc protection, the synthesis was continued in accordance with the process for Example 1 with reagent 3.

Reagent 3: 5-chloro-2-methoxybenzenesulfonyl chloride
MW=610.18 (calculated, monoisotopic); measured value (M+H)+: 611.4.

EXAMPLE 60

6-(4-Chlorobenzyl)-8-ethyl-1-(2-methoxy-5-methylbenzenesulfonyl)hexahydro-pyrazino[1,2-a]pyrimidine-4,7-dione Structure:

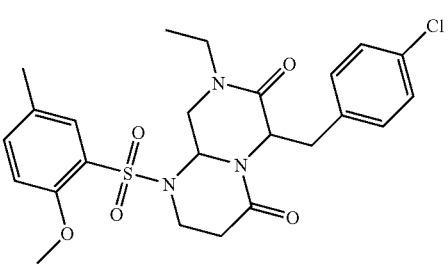

The compound in Example 60 was synthesized by the process described in Example 2 using the following reagents:

Reagent 1: ethylamine

Reagent 2: Fmoc-4-chlorophenylalanine

Reagent 3: 2-methoxy-5-methylbenzenesulfonyl chloride
MW=505.14 (calculated, monoisotopic); measured value (M+H)+: 506.3.

EXAMPLE 61

6-(4-Chlorobenzyl)-1-(2-methoxy-5-methylbenzenesulfonyl)-8-methylhexahydropyrazino[1,2-a]pyrimidine-4,7-dione Structure:

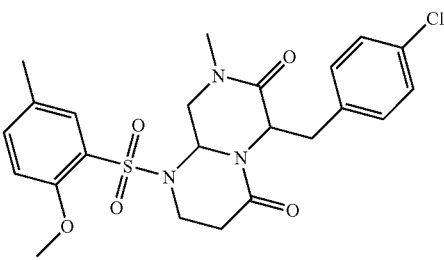

The compound in Example 61 was synthesized by the process described in Example 2 using the following reagents:

Reagent 1: methylamine

Reagent 2: Fmoc-4-chlorophenylalanine

Reagent 3: 2-methoxy-5-methylbenzenesulfonyl chloride
MW=491.13 (calculated, monoisotopic); measured value (M+H)+: 492.3.

EXAMPLE 62

6-(4-Chlorobenzyl)-8-isobutyl-1-(2-methoxy-5-methylbenzenesulfonyl)hexahydro-pyrazino[1,2-a]pyrimidine-4,7-dione Structure:

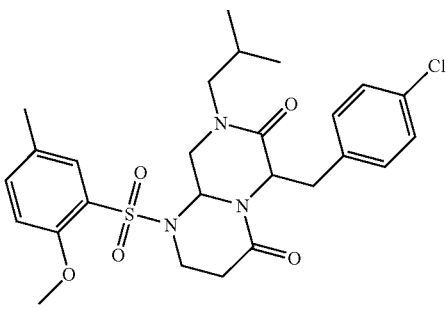

The compound in Example 62 was synthesized by the process described in Example 2 using the following reagents:

Reagent 1: isobutylamine

Reagent 2: Fmoc-4-chlorophenylalanine

Reagent 3: 2-methoxy-5-methylbenzenesulfonyl chloride
MW=533.18 (calculated, monoisotopic); measured value (M+H)$^+$: 534.3.

EXAMPLE 63

6-(4-Chlorobenzyl)-8-isobutyl-1-(2-methoxy-5-methylbenzenesulfonyl)hexahydro-pyrazino[1,2-a]pyrimidine-4,7-dione Structure:

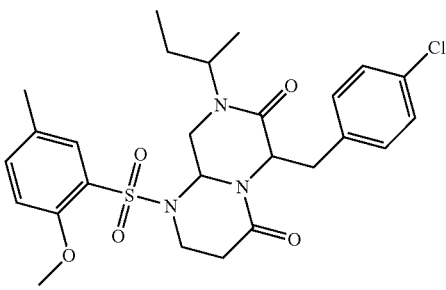

The compound in Example 63 was synthesized by the process described in Example 2 using the following reagents:

Reagent 1: 2-butylamine

Reagent 2: Fmoc-4-chlorophenylalanine

Reagent 3: 2-methoxy-5-methylbenzenesulfonyl chloride
MW=533.18 (calculated, monoisotopic); measured value (M+H)$^+$: 534.3.

EXAMPLE 64

1-(5-Chloro-2-methoxybenzenesulfonyl)-8-isopropyl-6-pyridin-3-ylmethylhexahydro-pyrazino[1,2-a]pyrimidine-4,7-dione Structure:

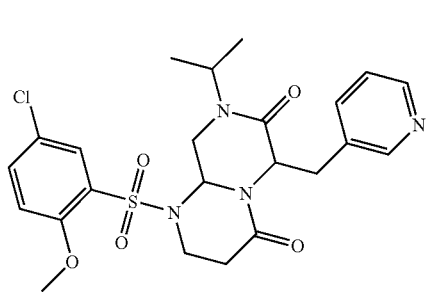

The compound in Example 64 was synthesized by the process described in Example 1 using the following reagents:

Reagent 1: isopropylamine

Reagent 2: Fmoc-3-pyridylalanine

Reagent 3: 5-chloro-2-methoxybenzenesulfonyl chloride
MW=506.14 (calculated, monoisotopic); measured value (M+H)$^+$: 507.3.

EXAMPLE 65

6-(4-Chlorobenzyl)-8-cyclopropyl-1-(2-methoxy-5-methylbenzenesulfonyl)hexahydro-pyrazino[1,2-a]pyrimidine-4,7-dione Structure:

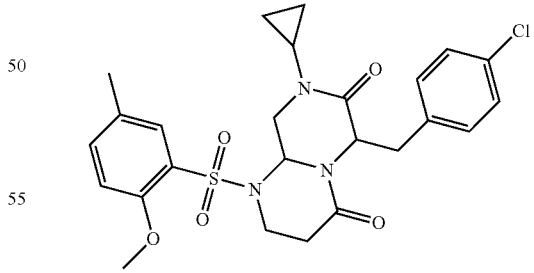

The compound in Example 65 was synthesized by the process described in Example 2 using the following reagents:

Reagent 1: cyclopropylamine

Reagent 2: Fmoc-4-chlorophenylalanine

Reagent 3: 2-methoxy-5-methylbenzenesulfonyl chloride
MW=517.14 (calculated, monoisotopic); measured value (M+H)$^+$: 518.3.

EXAMPLE 66

6-(4-Chlorobenzyl)-8-cyclopentyl-1-(2-methoxy-5-methylbenzenesulfonyl)hexahydro-pyrazino[1,2-a]pyrimidine-4,7-dione Structure:

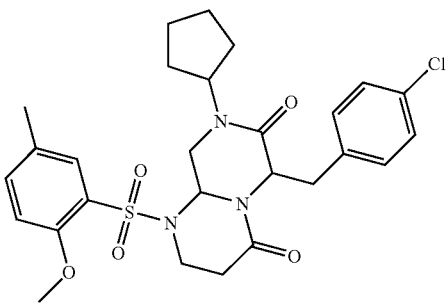

The compound in Example 66 was synthesized by the process described in Example 2 using the following reagents:

Reagent 1: cyclopentylamine

Reagent 2: Fmoc-4-chlorophenylalanine

Reagent 3: 2-methoxy-5-methylbenzenesulfonyl chloride
MW=545.18 (calculated, monoisotopic); measured value (M+H)$^+$: 546.3.

EXAMPLE 67

6-(4-Chlorobenzyl)-1-(2-methoxy-5-methylbenzenesulfonyl)-8-propylhexahydropyrazino[1,2-a]pyrimidine-4,7-dione Structure:

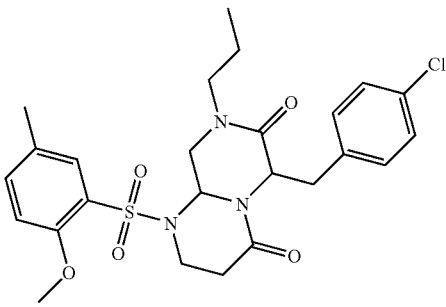

The compound in Example 67 was synthesized by the process described in Example 2 using the following reagents:

Reagent 1: n-propylamine

Reagent 2: Fmoc-4-chlorophenylalanine

Reagent 3: 2-methoxy-5-methylbenzenesulfonyl chloride
MW=519.16 (calculated, monoisotopic); measured value (M+H)$^+$: 520.3.

EXAMPLE 68

8-Allyl-6-(4-chlorobenzyl)-1-(2-methoxy-5-methylbenzenesulfonyl)hexahydro-pyrazino[1,2-a]pyrimidine-4,7-dione Structure:

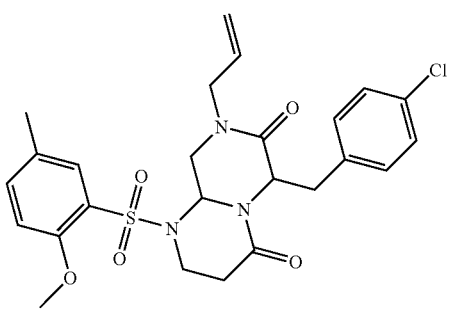

The compound in Example 68 was synthesized by the process described in Example 2 using the following reagents:

Reagent 1: allylamine

Reagent 2: Fmoc-4-chlorophenylalanine

Reagent 3: 2-methoxy-5-methylbenzenesulfonyl chloride
MW=517.14 (calculated, monoisotopic); measured value (M+H)$^+$: 518.2.

EXAMPLE 69

1-(5-Bromo-2-methoxybenzenesulfonyl)-6-(4-chlorobenzyl)-8-ethylhexahydropyrazino[1,2-a]pyrimidine-4,7-dione Structure:

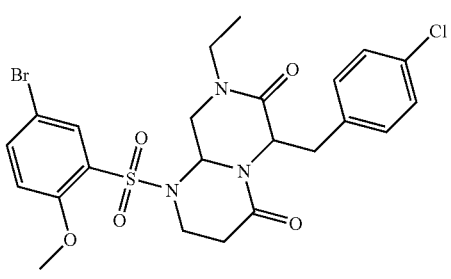

The compound in Example 69 was synthesized by the process described in Example 2 using the following reagents:

Reagent 1: ethylamine

Reagent 2: Fmoc-4-chlorophenylalanine

Reagent 3: 2-methoxy-5-bromobenzenesulfonyl chloride
MW=569.04 (calculated, monoisotopic); measured value (M+H)$^+$: 570.3.

EXAMPLE 70

6-(4-Chlorobenzyl)-1-(5-chloro-2-methoxybenzene-sulfonyl)-8-ethylhexahydropyrazino[1,2-a]pyrimidine-4,7-dione Structure:

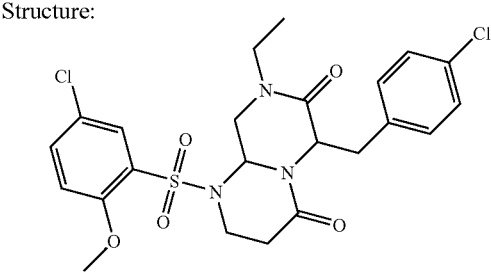

The compound in Example 70 was synthesized by the process described in Example 2 using the following reagents:

Reagent 1: ethylamine

Reagent 2: Fmoc-4-chlorophenylalanine

Reagent 3: 2-methoxy-5-chlorobenzenesulfonyl chloride
MW=525.09 (calculated, monoisotopic); measured value (M+H)$^+$: 526.3.

EXAMPLE 71

1-(4-Bromo-2-ethylbenzenesulfonyl)-6-(4-chlorobenzyl)-8-isopropylhexahydropyrazino[1,2-a]pyrimidine-4,7-dione Structure:

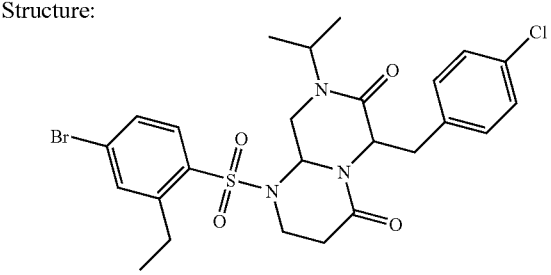

The compound in Example 71 was synthesized by the process described in Example 2 using the following reagents:

Reagent 1: isopropylamine

Reagent 2: Fmoc-4-chlorophenylalanine

Reagent 3: 5-bromo-2-ethylbenzenesulfonyl chloride
MW=581.08 (calculated, monoisotopic); measured value (M+H)$^+$: 582.3.

EXAMPLE 72

6-(4-Chlorobenzyl)-1-(2,5-dimethylbenzenesulfonyl)-8-ethylhexahydropyrazino-[1,2-a]pyrimidine-4,7-dione Structure:

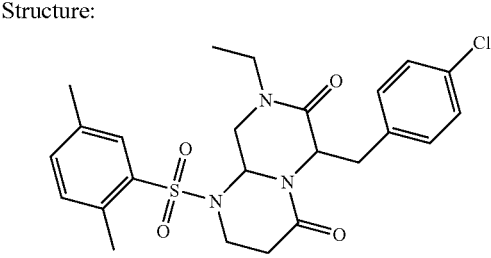

The compound in Example 72 was synthesized by the process described in Example 2 using the following reagents:

Reagent 1: ethylamine

Reagent 2: Fmoc-4-chlorophenylalanine

Reagent 3: 2,5-dimethylbenzenesulfonyl chloride
MW=489.15 (calculated, monoisotopic); measured value (M+H)$^+$: 490.3.

EXAMPLE 73

2-Chloro-5-[6-(4-chlorobenzyl)-8-isopropyl-4,7-dioxohexahydropyrazino[1,2-a]-pyrimidine-1-sulfonyl]benzenesulfonamide Structure:

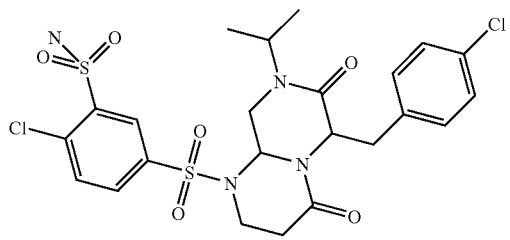

The compound in Example 73 was synthesized by the process described in Example 1 using the following reagents:

Reagent 1: isopropylamine

Reagent 2: Fmoc-4-chlorophenylalanine

Reagent 3: 4-chloro-2-sulfonylamidobenzenesulfonyl chloride
MW=588.07 (calculated, monoisotopic); measured value (M+H)$^+$: 589.3.

EXAMPLE 74

6-(4-Chlorobenzyl)-1-(2,4-dichloro-6-methylbenzenesulfonyl)-8-isopropylhexahydropyrazino[1,2-a]pyrimidine-4,7-dione Structure:

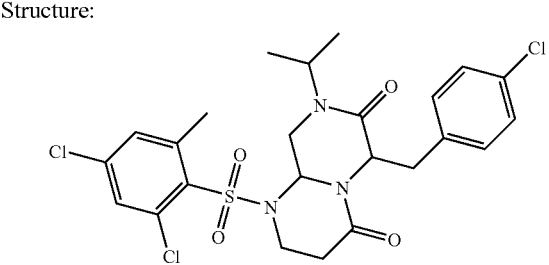

The compound in Example 74 was synthesized by the process described in Example 1 using the following reagents:

Reagent 1: isopropylamine

Reagent 2: Fmoc-4-chlorophenylalanine

Reagent 3: 2-methyl-4,6-dichlorobenzenesulfonyl chloride
MW=557.08 (calculated, monoisotopic); measured value (M+H)$^+$: 558.3.

EXAMPLE 75

6-(4-Chlorobenzyl)-8-isopropyl-1-(2-methoxy-4-methylbenzenesulfonyl)hexahydro-pyrazino[1,2-a]pyrimidine-4,7-dione Structure:

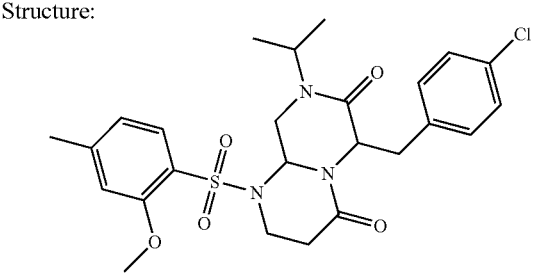

The compound in Example 75 was synthesized by the process described in Example 1 using the following reagents:

Reagent 1: isopropylamine

Reagent 2: Fmoc-4-chlorophenylalanine

Reagent 3: 2-methoxy-4-methylbenzenesulfonyl chloride
MW=519.16 (calculated, monoisotopic); measured value (M+H)+: 520.3.

EXAMPLE 76

6-(4-Chlorobenzyl)-8-isopropyl-1-(4-methoxybenzenesulfonyl)hexahydropyrazino[1,2-a]-pyrimidine-4,7-dione Structure:

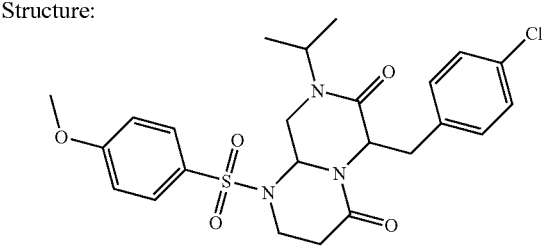

a) 3-(4-Chlorophenyl)-N-(2,2-diethoxyethyl)-N-isopropyl-2-[3-(4-methoxybenzene-sulfonylamino)propionylamino]propionamide 52 mg of EDC, 45 mg of HOBt and 100 µl of N-ethylmorpholine are added to a solution of 124 mg of 3-(4-methoxybenzenesulfonylamino)propionic acid in 1 ml of DMF. A solution of 100 mg of 2-amino-3-(4-chlorophenyl)-N-(2,2-diethoxyethyl)-N-isopropylpropionamide in 1 ml of DMF is added dropwise thereto, and the mixture is left to stir for 12 h. The reaction solution is filtered, mixed with ethyl acetate and then extracted with 5% aqueous sodium bicarbonate solution and aqueous sodium chloride solution. Drying of the organic phase with Chromabond XTR is followed by concentration under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=598.16 (calculated); measured value (M-C₂H₆O+H)+: 552.1 b) 6-(4-Chlorobenzyl)-8-isopropyl-1-(4-methoxy-benzenesulfonyl)hexahydro-pyrazino[1,2-a]pyrimidine-4,7-dione A solution of 167 mg of 3-(4-chlorophenyl)-N-(2,2-diethoxyethyl)-N-isopropyl-2-[3-(4-methoxybenzenesulfonylamino)propionylamino]propionamide in 3 ml of formic acid is stirred at room temperature for 12 h. The reaction solution is concentrated under reduced pressure, and the residue is separated by HPLC (Knauer Eurospher-100-10-C18, water (0.1% trifluoroacetic acid)/acetonitrile (0.1% trifluoroacetic acid)=80/20 →10/90). The desired product is obtained with MW=506.02 (calculated); measured value (M+H)+: 506.34

EXAMPLE 77

1-(4-Chlorobenzenesulfonyl)-6-(4-chlorobenzyl-8-isopropylhexahydropyrazino-[1,2-a]pyrimidine-4,7-dione Structure:

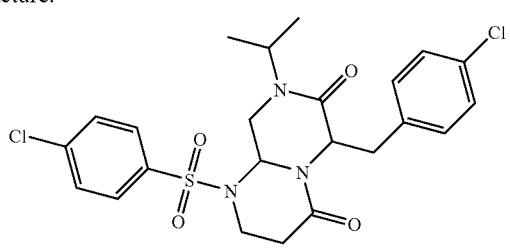

a) 3-(4-Chlorophenyl)-N-(2,2-diethoxyethyl)-N-isopropyl-2-[3-(4-chlorobenzene-sulfonylamino)propionylamino]propionamide Synthesis takes place in analogy to Example 76a) starting from 3-(4-chloro-benzenesulfonylamino)propionic acid. The desired product is obtained with MW=602.58 (calculated); measured value (M-C₂H₆O+H)+: 556.1 b) 6-(4-Chlorobenzyl)-8-isopropyl-1-(4-chlorobenzenesulfonyl)hexahydro-pyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(4-chlorobenzenesulfonylamino)propionylamino]-propionamide. The desired product is obtained with MW=510.44 (calculated); measured value (M+H)+: 510.30

EXAMPLE 78

6-(4-Chlorobenzyl)-1-(3,4-dimethoxybenzenesulfonyl)-8-isopropylhexahydropyrazino-[1,2-a]pyrimidine-4,7-dione Structure:

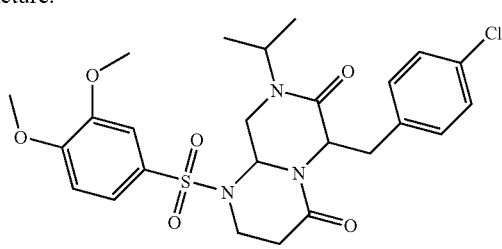

a) 3-(3,4-Dimethoxybenzenesulfonylamino)propionic acid

A solution of 3.8 g of 3,4-dimethoxybenzenesulfonyl chloride in 5 ml of dioxane is added dropwise to a solution of 1.5 g of 3-aminopropionic acid in 20 ml of 1N NaOH solution.

The mixture is left to stir while controlling the pH (pH>7) for 12 h, the pH is reduced below 7 by adding citric acid, and the reaction solution is then extracted with methylene chloride. The organic phase is dried over magnesium sulfate, concentrated under reduced pressure and employed without further purification in the next reaction step. The desired product is obtained with MW=289.31 (calculated); measured value (M+H)$^+$: 290.1 b) 3-(3,4-Dimethoxyphenyl)-N-(2,2-diethoxyethyl)-N-isopropyl-2-[3-(4-chloro-benzenesulfonylamino)propionylamino]propionamide Synthesis takes place in analogy to Example 76a) starting from 3-(3,4-dimethoxy-benzenesulfonylamino)propionic acid. The desired product is obtained with MW=628.19 (calculated); measured value (M+H)$^+$: 582.3 c) 6-(4-Chlorobenzyl)-1-(3,4-dimethoxybenzenesulfonyl)-8-isopropylhexahydropyrazino[1,2-a]pyrimidine-4,7-dione Synthesis takes place in analogy to Example 76b) starting from 3-(3,4-dimethoxyphenyl)-N-(2,2-diethoxyethyl)-N-isopropyl-2-[3-(4-chlorobenzenesulfonylamino)propionylamino]-propionamide. The desired product is obtained with MW=536.05 (calculated); measured value (M+H)$^+$: 536.36

EXAMPLE 79

1-(3-Chlorobenzenesulfonyl)-6-(4-chlorobenzyl)-8-isopropylhexahydropyrazino-[1,2-a]pyrimidine-4,7-dione Structure:

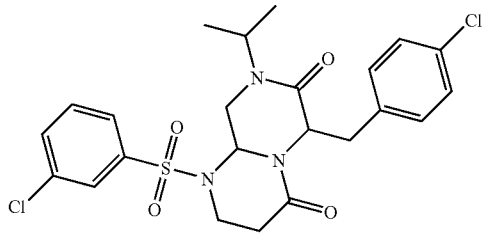

a) 3-(2-Chlorobenzenesulfonylamino)propionic acid

Synthesis takes place in analogy to Example 78a) starting from 2-chlorobenzenesulfonyl chloride. The desired product is obtained with MW=263.70 (calculated); measured value (M+H)$^+$: 264.05 b) 3-(4-Chlorophenyl)-N-(2,2-diethoxyethyl)-N-isopropyl-2-[3-(2-chloro-benzenesulfonylamino)propionylamino]propionamide Synthesis takes place in analogy to Example 76a) starting from 3-(2-chlorobenzene-sulfonylamino)propionic acid. The desired product is obtained with product with MW=602.58 (calculated); measured value (M-C$_2$H$_6$O+H)$^+$: 556.7 c) 1-(3-Chlorobenzenesulfonyl)-6-(4-chlorobenzyl)-8-isopropylhexahydropyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(2-chlorobenzenesulfonylamino)propionyl-amino]propionamide. The desired product is obtained with MW=510.44 (calculated); measured value (M+H)$^+$: 510.10

EXAMPLE 80

6-(4-Chlorobenzyl)-1-(4-fluorobenzenesulfonyl)-8-isopropylhexahydropyrazino-[1,2-a]pyrimidine-4,7-dione Structure:

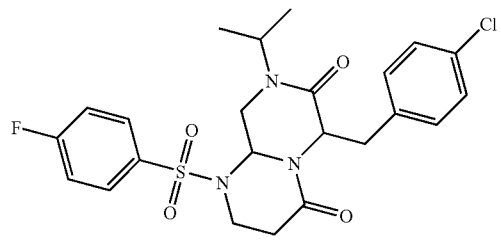

a) 3-(4-Chlorophenyl)-N-(2,2-diethoxyethyl)-N-isopropyl-2-[3-(4-fluorobenzene sulfonylamino)propionylamino]propionamide Synthesis takes place in analogy to Example 78) starting from 3-(4-fluorobenzene-sulfonylamino)propionic acid. The desired product is obtained with MW=586.13 (calculated); measured value (M-C$_2$H$_6$O+H)$^+$: 540.7 b) 6-(4-Chlorobenzyl)-8-isopropyl-1-(4-fluorobenzenesulfonyl)hexahydropyrazino-[1,2-a]pyrimidine-4, 7-dione Synthesis takes place in analogy to Example 76b) starting from 3-(4-chlorophenyl)-N-(2,2-diethoxyethyl)-N-isopropyl-2-[3-(4-fluorobenzenesulfonylamino)-propionylamino] propionamide. The desired product is obtained with MW=493.99 (calculated); measured value (M+H)$^+$: 494.13

EXAMPLE 81

6-(4-Chlorobenzyl)-1-(2,5-dimethoxybenzenesulfonyl)-8-isopropylhexahydropyrazino[1,2-a]pyrimidine-4,7-dione Structure:

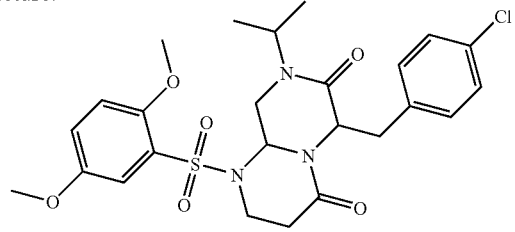

a) 3-(2,5-Dimethoxybenzenesulfonylamino)propionic acid

Synthesis takes place in analogy to Example 78a) starting from 2,5-dimethoxy-benzenesulfonyl chloride. The desired product is obtained with MW=289.31 (calculated); measured value (M+H)$^+$: 290.1 b) 3-(2,5-Dimethoxyphenyl)-N-(2,2-diethoxyethyl)-N-isopropyl-2-[3-(4-chloro-benzenesulfonylamino)propionylamino]propionamide Synthesis takes place in analogy to Example 76a) starting from 3-(2,5-dimethoxy-benzenesulfonylamino)propionic acid. The desired product is obtained with MW=628.19 (calculated); measured value (M-C₂H₆O+H)⁺: 582.7 c) 6-(4-Chlorobenzyl)-1-(2,5-dimethoxybenzenesulfonyl)-8-isopropylhexahydropyrazino[1,2-a]pyrimidine-4,7-dione Synthesis takes place in analogy to Example 76b) starting from 3-(2,5-dimethoxyphenyl)-N-(2,2-diethoxyethyl)-N-isopropyl-2-[3-(4-chlorobenzenesulfonylamino)propionylamino]-propionamide. The desired product is obtained with MW=536.05 (calculated); measured value (M+H)⁺: 536.16

EXAMPLE 82

6-(4-Chlorobenzyl)-1-(3-fluorobenzenesulfonyl)-8-isopropylhexahydropyrazino-[1,2-a]pyrimidine-4,7-dione Structure:

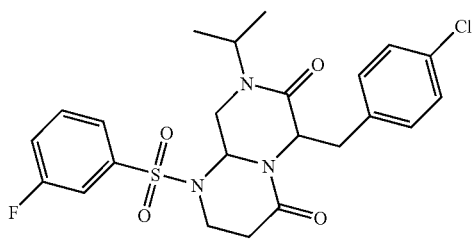

a) 3-(3-Fluorobenzenesulfonylamino)propionic acid

Synthesis takes place in analogy to Example 78a) starting from 3-fluorobenzenesulfonyl chloride. The desired product is obtained with MW=247.25 (calculated); measured value (M+H)⁺: 248.05 b) 3-(4-Chlorophenyl)-N-(2,2-diethoxyethyl)-N-isopropyl-2-[3-(3-fluoro-benzenesulfonylamino)propionylamino]propionamide Synthesis takes place in analogy to Example 76a) starting from 3-(3-fluorobenzene-sulfonylamino)propionic acid. The desired product is obtained with MW=586.13 (calculated); measured value (M-C₂H₆O+H)⁺: 540.7 c) 6-(4-Chlorobenzyl)-8-isopropyl-1-(3-fluorobenzenesulfonyl)hexahydro-pyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(3-fluorobenzenesulfonylamino)propionylamino]-propionamide. The desired product is obtained with MW=493.99 (calculated); measured value (M+H)⁺: 494.25

EXAMPLE 83

1-Benzenesulfonyl-6-(4-chlorobenzyl)-8-isopropyl-hexahydropyrazino[1,2-a]pyrimidine-4,7-dione Structure:

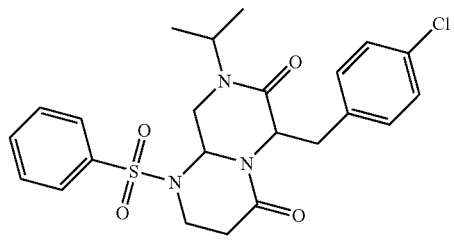

a) 3-(4-Chlorophenyl)-N-(2,2-diethoxyethyl)-N-isopropyl-2-[3-(benzenesulfonyl-amino)propionylamino]propionamide Synthesis takes place in analogy to Example 78a) starting from 3-(benzenesulfonylamino)propionic acid. The desired product is obtained with MW=568.13 (calculated); measured value (M-C₂H₆O+H)⁺: 522.7 b) 6-(4-Chlorobenzyl)-8-isopropyl-1-(benzenesulfonyl)hexahydropyrazino[1,2-a]-pyrimidine-4,7-dione Synthesis takes place in analogy to Example 76b) starting from 3-(4-chlorophenyl)-N-(2,2-diethoxyethyl)-N-isopropyl-2-[3-(benzenesulfonylamino)propionylamino]propionamide. The desired product is obtained with MW=475.99 (calculated); measured value (M+H)⁺: 476.14

EXAMPLE 84

6-(4-Chlorobenzyl)-1-(2-fluorobenzenesulfonyl)-8-isopropylhexahydropyrazino-[1,2-a]pyrimidine-4,7-dione Structure:

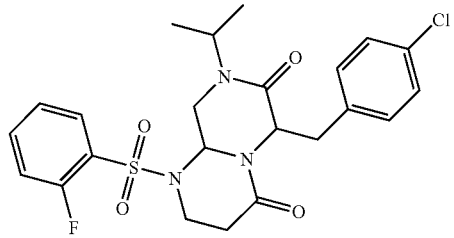

a) 3-(2-Fluorobenzenesulfonylamino)propionic acid

Synthesis takes place in analogy to Example 78a) starting from 2-fluorobenzenesulfonyl chloride. The desired product is obtained with MW=247.25 (calculated); measured value (M+H)⁺: 248.05 b) 3-(4-Chlorophenyl)-N-(2,2-diethoxyethyl)-N-isopropyl-2-[3-(2-fluorobenzene-sulfonylamino)propionylamino]propionamide Synthesis takes place in analogy to Example 76a) starting from 3-(2-fluoro-benzenesulfonylamino)propionic acid. The desired product is obtained with MW=586.13 (calculated); measured value (M-C₂H₆O+H)⁺: 540.7 c) 6-(4-Chlorobenzyl)-8-isopropyl-1-(2-fluorobenzenesulfonyl)hexahydro-pyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(2-fluorobenzenesulfonylamino)propionylamino]-propionamide. The desired product is obtained with MW=493.99 (calculated); measured value (M+H)$^+$: 494.13

EXAMPLE 85

6-(4-Chlorobenzyl)-1-(2,4-difluorobenzenesulfonyl)-8-isopropylhexahydropyrazino-[1,2-a]pyrimidine-4,7-dione Structure:

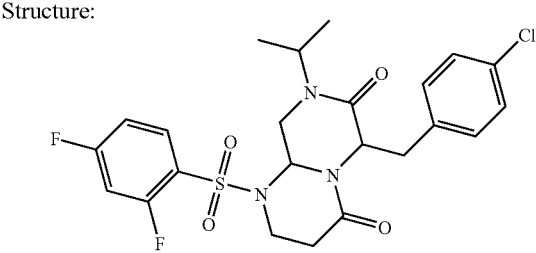

a) 3-(2,4-Difluorobenzenesulfonylamino)propionic acid

Synthesis takes place in analogy to Example 78a) starting from 2,4-difluoro-benzenesulfonyl chloride. The desired product is obtained with MW=265.25 (calculated); measured value (M+H)$^+$: 266.05 b) 3-(4-Chlorophenyl)-N-(2,2-diethoxyethyl)-N-isopropyl-2-[3-(2,4-difluoro-benzenesulfonylamino)propionylamino]propionamide Synthesis takes place in analogy to Example 76a) starting from 3-(2,4-difluoro-benzenesulfonylamino)propionic acid. The desired product is obtained with MW=604.13 (calculated); measured value (M-C$_2$H$_6$O+H)$^+$: 558.7 c) 6-(4-Chlorobenzyl)-8-isopropyl-1-(2,4-difluorobenzenesulfonyl)hexahydro-pyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(2,4-difluorobenzenesulfonylamino)-propionylamino]propionamide. The desired product is obtained with MW=511.99 (calculated); measured value (M+H)$^+$: 512.12

EXAMPLE 86

6-(4-Chlorobenzyl)-1-(3,4-difluorobenzenesulfonyl)-8-isopropylhexahydropyrazino-[1,2-a]pyrimidine-4,7-dione Structure:

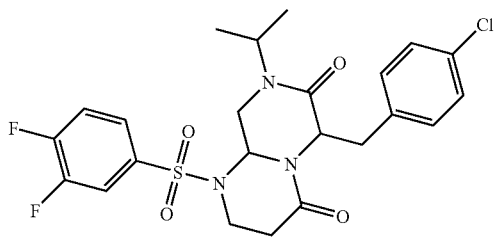

a) 3-(3,4-Difluorobenzenesulfonylamino)propionic acid

Synthesis takes place in analogy to Example 78a) starting from 3,4-difluoro-benzenesulfonyl chloride. The desired product is obtained with MW=265.25 (calculated); measured value (M+H)$^+$: 266.05 b) 3-(4-Chlorophenyl-N-(2,2-diethoxyethyl)-N-isopropyl-2-[3-(3,4-difluorobenzene-sulfonylamino) propionylamino]propionamide Synthesis takes place in analogy to Example 76a) starting from 3-(3,4-difluoro-benzenesulfonylamino)propionic acid. The desired product is obtained with MW=604.13 (calculated); measured value (M+H)$^+$: 558.7 c) 6-(4-Chlorobenzyl)-8-isopropyl-1-(3,4-difluorobenzenesulfonyl)hexahydro-pyrazino[1,2-a]pyrimidine-4,7-dione Synthesis takes place in analogy to Example 76b) starting from 3-(4-chlorophenyl)-N-(2,2-diethoxyethyl)-N-isopropyl-2-[3-(3,4-difluorobenzenesulfonylamino)-propionylamino]propionamide. The desired product is obtained with MW=511.99 (calculated); measured value (M+H)$^+$: 512.12

We claim:
1. A method of treating obesity comprising administering to a patient in need thereof a compound of Formula I

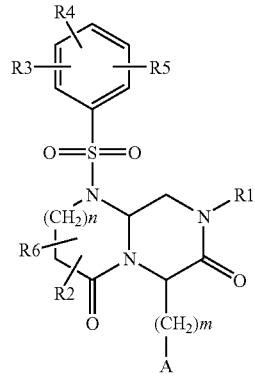

wherein
A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, NO$_2$, CF$_3$, OCF$_3$, CN, (C$_1$-C$_6$)-alkyl, aryl, CON(R11)(R12), N(R13)(R14), OH, O—(C$_1$-C$_6$)-alkyl, S—(C$_1$-C$_6$)-alkyl, N(R15)CO(C$_1$-C$_6$)-alkyl or COO—(C$_1$-C$_6$)-alkyl;
R11, R12, R13, R14, R15 are each independently H, (C$_1$-C$_6$)-alkyl or a heterocycle;
n is 1;
m is 0, 1, 2, 3, 4, 5 or 6;
R1 is R8, (C$_1$-C$_6$)-alkylene-R8, (C$_2$-C$_6$)-alkenylene-R9, (SO$_2$)—R8, (SO$_2$)—(C$_1$-C$_6$)-alkylene-R8, (SO$_2$)—(C$_2$-C$_6$)-alkenylene-R9, (C=O)—R8, (C=O)—(C$_1$-C$_6$)-alkylene-R8, (C=O)NH—R8, (C=O)—(C$_2$-C$_6$)-alkenylene-R9, (C=O)—NH—(C$_1$-C$_6$)-alkylene-R8, (C=O)—NH—(C$_2$-C$_6$)-alkenylene-R9, COO—R8, COO—(C$_1$-C$_6$)-alkylene-R8, COO—(C$_2$-C$_6$)-alkenylene-R9, alkynylene-R9 or (C$_1$-C$_4$-alkyl)-heterocycle, wherein the alkylene component of said (C$_1$-C$_6$)-alkylene-R8, (C$_2$-C$_6$)-alkenylene-R9, (SO$_2$)—(C$_1$-C$_6$)-alkylene-R8, (SO$_2$)—(C$_2$-C$_6$)-alkenylene-R9, (C=O)—(C$_1$-C$_6$)-alkylene-R8, (C=O)—(C$_2$-C$_6$)-alkenylene-R9, (C=O)—NH—(C$_1$-C$_6$)-alkylene-R8, (C=O)—NH—($C_2$-$C_6$)-alkenylene-R9, COO—($C_1$-$C_6$)-alkylene-R8, COO—($C_2$-$C_6$)-alkenylene-R9 and alkynylene-R9 groups is optionally substituted by F;

R8, R9 are each independently H, F, Cl, Br, I, OH, $CF_3$, aryl, heterocycle or ($C_3$-$C_8$)-cycloalkyl, wherein said aryl, heterocycle and ($C_3$-$C_8$)-cycloalkyl groups are optionally mono-, di- or tri-substituted by F, Cl, Br, I, OH, $CF_3$, $NO_2$, CN, $OCF_3$, O—($C_1$-$C_6$)-alkyl, ($C_1$-$C_6$)-alkyl, $NH_2$, CON(R11)(R12), N(R13)(R14), $SO_2$—$CH_3$, COOH, COO—($C_1$-$C_6$)-alkyl or $CONH_2$;

R2 is H, F, Cl, Br, I, OH, $CF_3$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, aryl, O-aryl, ($C_1$-$C_8$)-alkylene-aryl, O—($C_1$-$C_8$)-alkylene-aryl, S-aryl, CON(R11)(R12), ($C_1$-$C_6$)-alkyl-N(R13)(R14), COOH, COO—($C_1$-$C_6$)-alkyl, COO—($C_2$-$C_6$)-alkenyl, CO—N(($C_1$-$C_6$)-alkyl)$_2$ or heterocycle, with the proviso that said heterocycle may not be bonded via a nitrogen atom;

R3, R4, R5 are each independently H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, aryl, O-aryl ($C_1$-$C_8$)-alkylene-aryl, O—($C_1$-$C_8$)-alkylene-aryl, S-aryl, N(($C_1$-$C_6$)-alkyl)$_2$, $SO_2$—$CH_3$, COOH, COO—($C_1$-$C_6$)-alkyl or CO—N(($C_1$-$C_6$)-alkyl)$_2$;

R6 is H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(($C_1$-$C_6$)-alkyl)$_2$, $SO_2$—$CH_3$, COOH, COO—($C_1$-$C_6$)-alkyl or CO—N(($C_1$-$C_6$)-alkyl)$_2$;

or a pharmaceutically acceptable salt thereof.

2. A method of reducing weight in mammals comprising administering to a patient in need thereof a compound of Formula I of claim 1 or a pharmaceutically acceptable salt thereof.

* * * * *

UNITED STATES PATENT AND TRADEMARK OFFICE
CERTIFICATE OF CORRECTION

PATENT NO. : 7,750,005 B2
APPLICATION NO. : 12/124503
DATED : July 6, 2010
INVENTOR(S) : Stefanie Flohr et al.

Page 1 of 2

It is certified that error appears in the above-identified patent and that said Letters Patent is hereby corrected as shown below:

Title Pg, Item (56), under "Foreign Patent Documents", line 1, delete "WO 97/28265" and insert -- WO 97/26265 --, therefor.

In column 2, line 2, delete "alkylene" and insert -- alkynylene --, therefor.

In column 2, line 46, delete "allyl," and insert -- alkyl, --, therefor.

In column 3, line 43, delete "$N_2$," and insert -- $NH_2$, --, therefor.

In column 3, line 47, delete "(R3)" and insert -- (R13) --, therefor.

In column 4, line 32-33, delete "benzimidazalinyl" and insert -- benzimidazolinyl --, therefor.

In column 7, line 22, delete "gun" and insert -- gum --, therefor.

In column 7, line 29, delete "adminstered" and insert -- administered --, therefor.

In column 9, line 11, delete "embodiment" and insert -- embodiment, --, therefor.

In column 9, line 19, delete "embodiment" and insert -- embodiment, --, therefor.

In column 10, line 2, delete "rampril," and insert -- ramipril, --, therefor.

In column 10, line 7, delete "19-th" and insert -- 19th --, therefor.

In column 14, line 4, delete "ammo-" and insert -- amino- --, therefor.

In column 16, line 55, delete "0.1-0.15M" and insert --0.1-0.15M) --, therefor.

Signed and Sealed this
Seventh Day of June, 2011

David J. Kappos
*Director of the United States Patent and Trademark Office*

CERTIFICATE OF CORRECTION (continued)
U.S. Pat. No. 7,750,005 B2

In column 18, line 54, delete "DMSO" and insert -- DMSO. --, therefor.

In column 19, line 9, delete "off" and insert -- off, --, therefor.

In column 23, line 27, delete "hydroxyphenyl-ethyl]" and insert -- hydroxyphenyl)ethyl] --, therefor.

In column 30, line 3, delete "Dimethylbenzenesulfonyl-8-isopropyl" and insert -- Dimethylbenzenesulfonyl)-8-isopropyl --, therefor.

In column 41, line 18, delete "reagents." and insert -- reagents: --, therefor.

In column 52, line 9, delete "chlorobenzyl-8-" and insert -- chlorobenzyl)-8- --, therefor.